United States Patent
Ashiwal et al.

(10) Patent No.: US 11,555,792 B2
(45) Date of Patent: *Jan. 17, 2023

(54) TERAHERTZ SPECTROSCOPY AND IMAGING IN DYNAMIC ENVIRONMENTS WITH PERFORMANCE ENHANCEMENTS USING AMBIENT SENSORS

(71) Applicant: Apple Inc., Cupertino, CA (US)

(72) Inventors: Vijendrakumar K. Ashiwal, San Jose, CA (US); Sireesha Ramisetti, Sunnyvale, CA (US); Chia-Chi Chen, Milpitas, CA (US); Vusthla Sunil Reddy, Cupertino, CA (US); Peter M. Agboh, Burlingame, CA (US)

(73) Assignee: Apple Inc., Cupertino, CA (US)

( * ) Notice: Subject to any disclaimer, the term of this patent is extended or adjusted under 35 U.S.C. 154(b) by 537 days.

This patent is subject to a terminal disclaimer.

(21) Appl. No.: 16/536,266

(22) Filed: Aug. 8, 2019

(65) Prior Publication Data

US 2021/0041376 A1 Feb. 11, 2021

(51) Int. Cl.
*G01N 22/00* (2006.01)
*G01N 33/00* (2006.01)
*G01S 13/88* (2006.01)

(52) U.S. Cl.
CPC ......... *G01N 22/00* (2013.01); *G01N 33/0027* (2013.01); *G01S 13/887* (2013.01)

(58) Field of Classification Search
CPC ...... G01N 22/00; G01S 13/887; G01S 13/888
See application file for complete search history.

(56) References Cited

U.S. PATENT DOCUMENTS 6,244,743 B1 * 6/2001 Bååth .................... G01N 22/00
374/161
6,690,817 B1 * 2/2004 Cabib .................... G01J 3/453
382/165

(Continued)

FOREIGN PATENT DOCUMENTS

CN 101566589 10/2009
CN 104870931 8/2015

(Continued)

OTHER PUBLICATIONS

Lin et al., "Gas recognition with terahertz time-domain spectroscopy and spectral catalog: a preliminary study," Terahertz Photonics, Nov. 29, 2007, pp. 1-9.

(Continued)

*Primary Examiner* — Peter M Bythrow
(74) *Attorney, Agent, or Firm* — Fish & Richardson P.C.

(57) ABSTRACT

Embodiments are disclosed for terahertz spectroscopy and imaging in dynamic environments. In an embodiment, a method comprises using a sensor of an electronic device to determine an orientation of the electronic device. A transmitter of the electronic device emits an electromagnetic (EM) wave in a terahertz (THz) frequency band into a dynamic environment according to a power duty cycle that is determined at least in part by the orientation. A receiver of the electronic device receives a reflected EM wave from the environment. A spectral response of the reflected EM wave is determined that includes absorption spectra that is indicative of the transmission medium in the environment. The absorption spectra are compared with known absorption spectra of target transmission mediums. Based on the comparing, a particular target transmission medium is identified as being the transmission medium in the environment, and (Continued)

a concentration level of the identified target transmission medium in the environment is determined.

18 Claims, 31 Drawing Sheets

(56) References Cited

U.S. PATENT DOCUMENTS

| | | | |
|---|---|---|---|
| 6,965,340 B1 | 11/2005 | Baharav et al. | |
| 7,283,242 B2 | 10/2007 | Thornton | |
| 7,411,195 B2 | 8/2008 | Narasako et al. | |
| 7,586,094 B2 | 9/2009 | Liu et al. | |
| 7,804,069 B2 | 9/2010 | Tribe | |
| 8,514,393 B2 | 8/2013 | Khan et al. | |
| 8,571,254 B2* | 10/2013 | Ogura | G07D 7/205 |
| | | | 382/100 |
| 8,716,666 B1 | 5/2014 | Demers et al. | |
| 8,941,828 B2 | 1/2015 | Loock et al. | |
| 9,239,287 B2 | 1/2016 | Chun et al. | |
| 9,322,716 B2 | 4/2016 | Kusukame et al. | |
| 9,599,555 B2 | 3/2017 | Richter et al. | |
| 10,352,849 B2 | 7/2019 | Watanabe et al. | |
| 11,099,072 B2 | 8/2021 | Ramisetti et al. | |
| 2004/0065831 A1* | 4/2004 | Federici | G01S 13/887 |
| | | | 250/341.1 |
| 2004/0155193 A1 | 8/2004 | Tran et al. | |
| 2005/0156120 A1* | 7/2005 | Arnone | G01N 21/3563 |
| | | | 250/492.2 |
| 2008/0116374 A1* | 5/2008 | Ouchi | G01S 13/887 |
| | | | 250/306 |
| 2008/0149819 A1 | 6/2008 | Zhdaneev | |
| 2009/0026374 A1 | 1/2009 | Kajii | |
| 2010/0072368 A1 | 3/2010 | Boegli et al. | |
| 2012/0050743 A1 | 3/2012 | Yanai et al. | |
| 2012/0099856 A1 | 4/2012 | Britz et al. | |
| 2012/0273681 A1 | 11/2012 | Schulkin et al. | |
| 2013/0050007 A1* | 2/2013 | Ammar | G01S 7/412 |
| | | | 367/93 |
| 2013/0053661 A1 | 2/2013 | Alberth et al. | |
| 2013/0121529 A1* | 5/2013 | Fleisher | G01S 13/89 |
| | | | 382/103 |
| 2015/0041658 A1 | 2/2015 | Chun et al. | |
| 2015/0062572 A1 | 3/2015 | Tharaldsen et al. | |
| 2015/0160181 A1* | 6/2015 | White | G01S 13/887 |
| | | | 702/22 |
| 2015/0276920 A1* | 10/2015 | Kim | G01S 7/354 |
| | | | 342/175 |
| 2015/0316511 A1* | 11/2015 | Guo | H04B 10/27 |
| | | | 398/140 |
| 2015/0369729 A1* | 12/2015 | Molter | G01N 21/3581 |
| | | | 250/339.07 |
| 2017/0059469 A1 | 3/2017 | Hutter | |
| 2017/0089829 A1 | 3/2017 | Bartholomew | |
| 2017/0363541 A1 | 12/2017 | Sandsten et al. | |
| 2018/0209848 A1 | 7/2018 | Shimura et al. | |
| 2018/0234176 A1 | 8/2018 | Kitazawa | |
| 2018/0321068 A1 | 11/2018 | Meribout et al. | |
| 2019/0113613 A1* | 4/2019 | Manneschi | G01S 13/887 |
| 2019/0196054 A1 | 6/2019 | Csutak | |
| 2019/0285747 A1 | 9/2019 | Yakymyshyn | |
| 2021/0041292 A1* | 2/2021 | Chen | G01J 3/021 |
| 2021/0041293 A1 | 2/2021 | Ramisetti et al. | |
| 2021/0041295 A1 | 2/2021 | Ramisetti et al. | |
| 2021/0318234 A1* | 10/2021 | Kawamae | G01N 21/3581 |

FOREIGN PATENT DOCUMENTS

| | | |
|---|---|---|
| CN | 106290228 | 1/2017 |
| CN | 107907499 | 4/2018 |
| CN | 109283141 | 1/2019 |
| KR | 20140007116 | 1/2014 |
| WO | WO 2009146561 | 12/2009 |

OTHER PUBLICATIONS

Li Li et al. "Optical imaging with scanning MEMS mirror—A single photodetector approached," Image Processing (ICIP), 16th IEEE International Conference on IEEE, Piscataway, NJ, USA, Nov. 7, 2009, pp. 2685-2688.

Bobin et al., "A fast and accurate first-order algorithm for compressed sensing," 16th IEEE International Conference on Image Processing (ICIP), Feb. 17, 2010, pp. 1457-1460.

* cited by examiner

| LOSS | CONTRIBUTING FACTORS | HOW DOES IT AFFECT? | EXPLANATION |
|---|---|---|---|
| ENVIRONMENT LOSS | DISTANCE | LOWERS THE SIGNAL TO NOISE RATIO OF THE SYSTEM | REFLECTIVE ENERGY IS A FUNCTION OF DISTANCE. AS DISTANCE INCREASES, RECEIVED SIGNAL STRENGTH DECREASES |
| | ATMOSPHERIC ABSORPTION LOSS | | THz WAVES ARE ABSORBED IN THE ATMOSPHERE AS THEY PROPAGATE. HENCE LONGER THE PATH LENGTH, MORE IS THE ABSORPTION |
| | ANGLE OF INCIDENCE | | DEPENDING ON THE CERTAIN ANGLE AT WHICH THE TRANSMITTED SIGNAL HITS THE TARGET, THE RECEIVED SIGNAL STRENGTH MAY DEGRADE AS COMPARED TO OTHER ANGLES |
| | NATURE OF THE REFLECTIVE MATERIAL (REFRACTIVE INDEX) | | SOME COMMON MATERIALS LIKE PLYWOOD, PINE WOOD, BRICK HAVE LOWER REFRACTIVE INDEX WHICH LEADS TO HIGHER REFLECTIVE LOSS |
| SYSTEM LOSS | LOSS DUE TO FREQUENCY RANGE | INACCURATE GAS CONCENTRATION PREDICTION AT HIGH FREQUENCY | PATH LOSS IS A FUNCTION OF DISTANCE, HIGHER THz FREQUENCY WILL EXPERIENCE MORE LOSS AS COMPARED TO LOWER FREQUENCY, WHICH CAN HINDER THE GAS CONCENTRATION ACCURACY AT HIGHER FREQUENCY |

FIG. 3

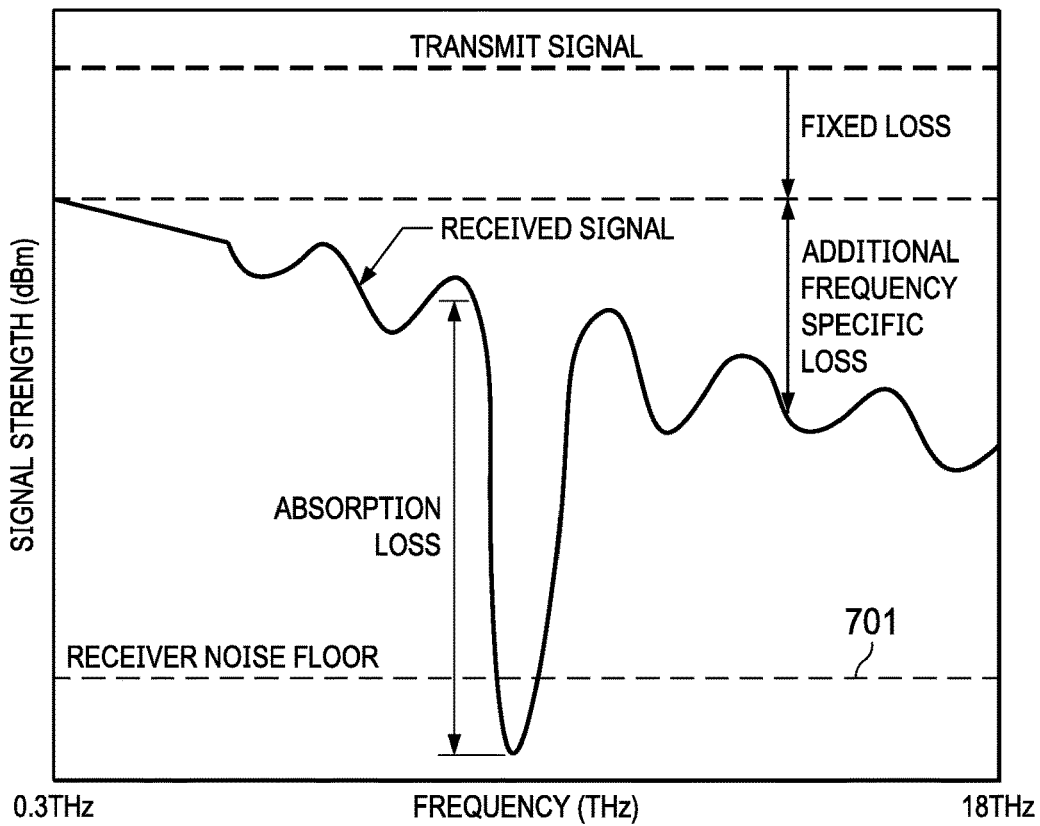
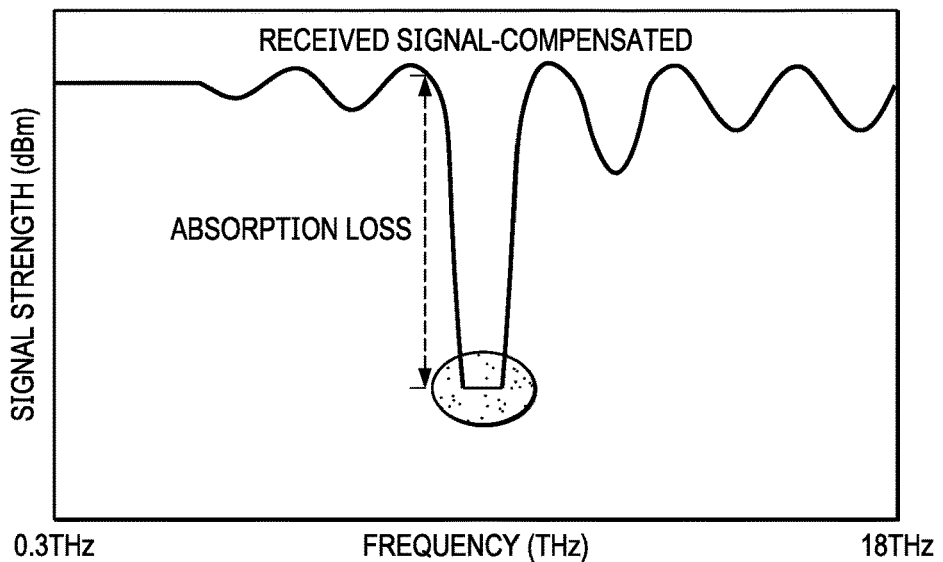

| PATH LENGTH | ABSORPTION LOSS | TARGET GAS CONCENTRATION |
|---|---|---|
| D/n... D | 1% | 1 |
| | 5% | 5 |
| | 10% | 10 |
| | 20% | 20 |
| | ..... | ..... |
| | 99% | X |

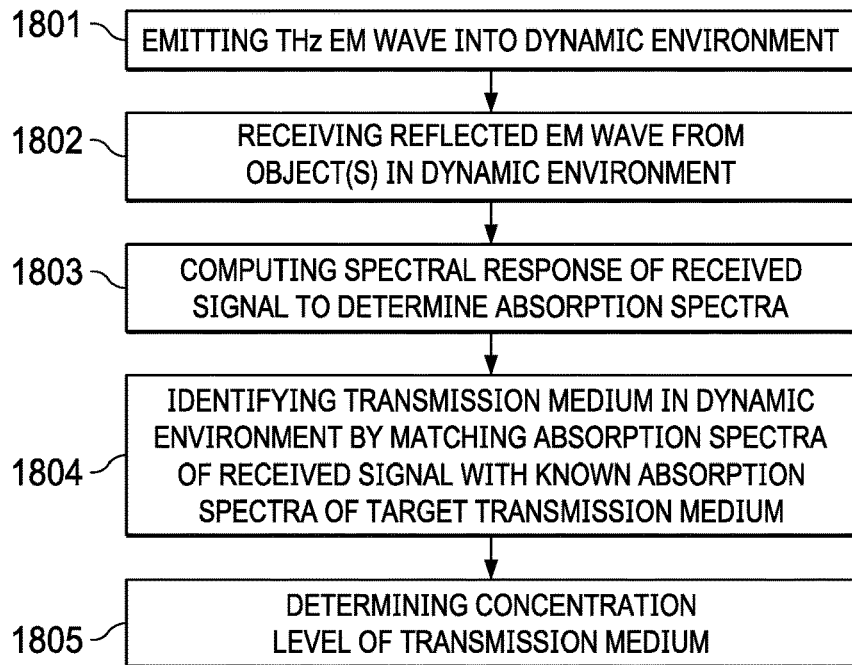
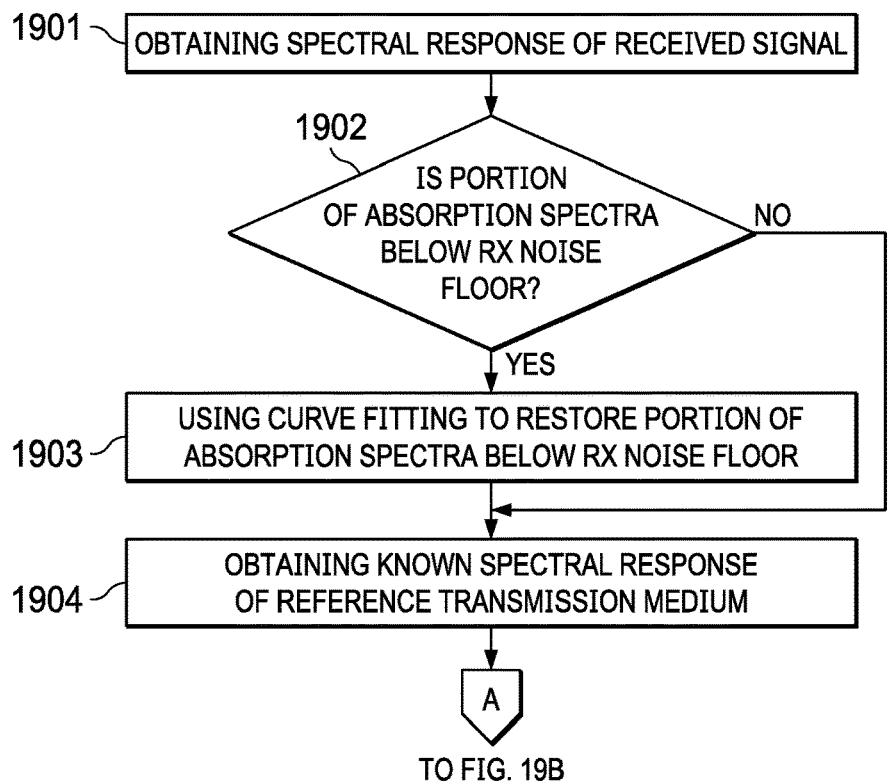

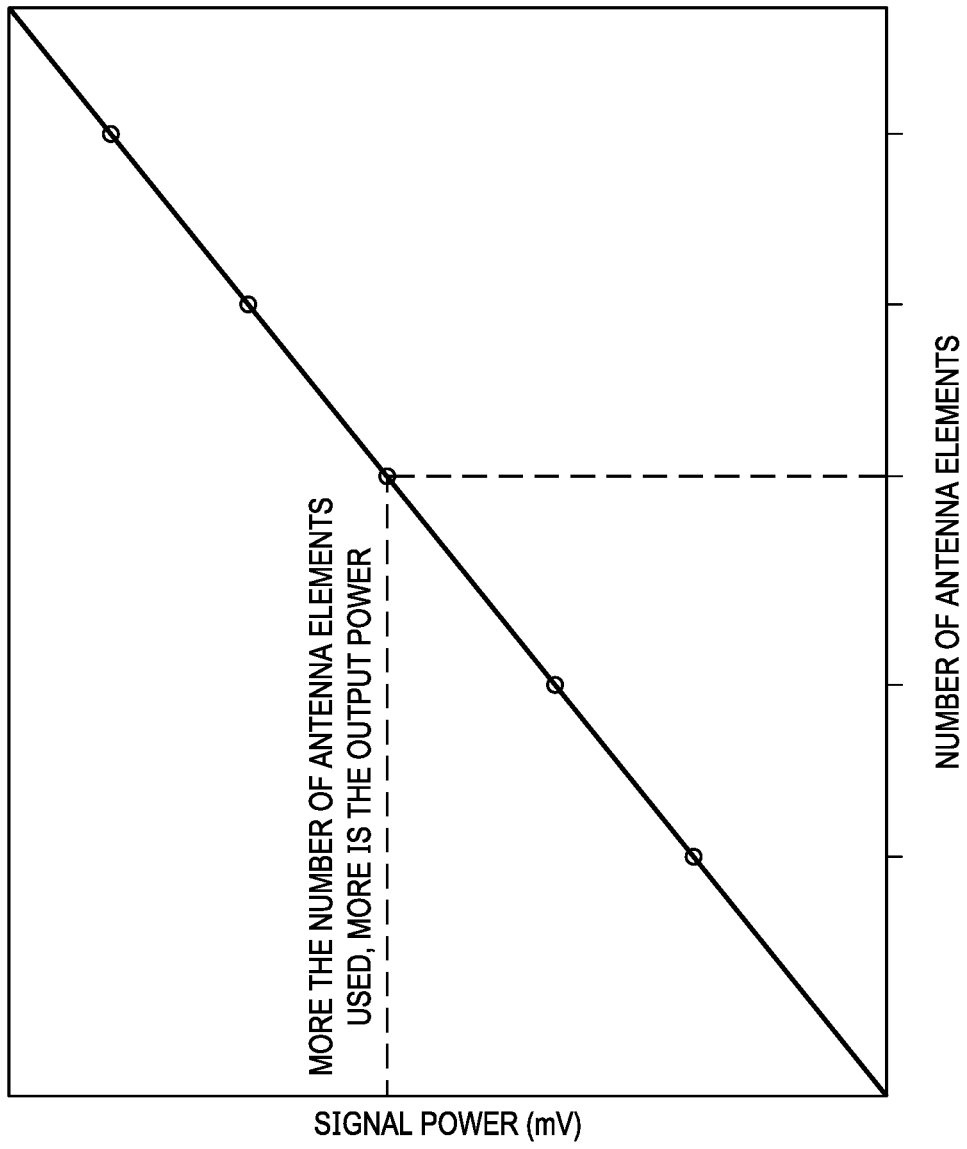

TERAHERTZ SPECTROSCOPY AND IMAGING IN DYNAMIC ENVIRONMENTS WITH PERFORMANCE ENHANCEMENTS USING AMBIENT SENSORS

TECHNICAL FIELD

This disclosure relates generally to terahertz (THz) spectroscopy and imaging.

BACKGROUND

Today's sensor technologies (e.g., metal-oxide (MOX) gas sensors, electrochemical gas sensors) can detect a few gases but have several disadvantages. For example, integrating a gas sensor on an electronic device requires an aperture or opening to allow air to flow onto the gas sensor so that the gas can be detected. The design of an aperture into a consumer electronic device poses several challenges. The aperture may degrade water resistivity of the device. Also, the size of the aperture may be constrained due to a tradeoff between form factor and gas detection capability. In addition to aperture constraints, the number of gases detected by a given sensor is limited and one sensor cannot detect gas, liquid and solid materials. Integrating multiple sensors on the consumer electronic device to detect gas, liquid and solid materials would increase the size and cost of the consumer electronic device. Also, many of today's gas sensors have a high idle-time current consumption to maintain the properties of the sensor. For example, MOX gas sensors have heating elements that are used to maintain a certain temperature of the sensor at all times. Also, the accuracy of today's gas sensors drift over time requiring periodic calibration.

In addition to detecting the presence of gas, health/quality of liquid or solid materials in an environment, there is need for imaging applications on consumer electronic devices related to health monitoring, such as detecting skin cancer and other skin disorders. The conventional image sensors (e.g., CMOS image sensors) found on consumer electronic devices, however, are incapable of performing such health monitoring applications.

SUMMARY

Embodiments are disclosed for THz spectroscopy and imaging in dynamic environments with performance enhancements using ambient sensors.

In an embodiment, a method comprises obtaining, from a sensor of an electronic device, sensor data. One or more processors of the electronic device determine an orientation of the electronic device based on the sensor data. A transmitter of the electronic device emits a electromagnetic (EM) wave in a terahertz (THz) frequency band into a dynamic environment that includes a transmission medium that changes over time. The EM wave is emitted according to a power duty cycle that is determined at least in part by the orientation of the electronic device. A receiver of the electronic device receives a reflected EM wave reflected off at least one object in the environment. One or more processors of the electronic device determine a spectral response of a received signal indicative of the reflected EM wave. The spectral response includes absorption spectra at a frequency in the THz frequency band that is indicative of the transmission medium in the environment. The one or more processors compare the absorption spectra with known absorption spectra of target transmission mediums. Based on results of the comparing, the one or more processors identify a particular target transmission medium as being the transmission medium in the environment, and determine a concentration level of the identified target transmission medium in the environment.

In an embodiment, a method comprises: emitting, by a transmitter of an electronic device, an EM wave in a THz frequency band into a dynamic environment, the emitting including sweeping transmission of the EM wave through a plurality of angles; for each angle of the plurality of angles: receiving, by a receiver of the electronic device, an EM wave reflected from the environment; determining, by the receiver, a first received signal strength of the received EM wave; and storing the angle and first received signal strength in a data structure that includes a plurality of angles and corresponding received signal strengths; determining, from the plurality of angles, a particular angle having the highest received signal strength; adapting the transmitter to emit the EM wave in accordance with the particular angle; receiving, by the receiver, a reflected EM wave reflected off at least one object in the environment; determining, by one or more processors of the electronic device, a spectral response of a received signal indicative of the reflected EM wave, the spectral response including absorption spectra at a frequency in the THz frequency band that is indicative of the transmission medium in the environment; comparing, by the one or more processors, the absorption spectra with known absorption spectra of target transmission mediums; identifying, by the one or more processors and based on results of the comparing, a particular target transmission medium as being the transmission medium in the environment; and determining, by the one or more processors, a concentration level of the identified target transmission medium in the environment.

In an embodiment, a method comprising: emitting, by a transmitter of the electronic device, an EM wave in a THz frequency band, the EM wave being emitted into a dynamic environment that includes a transmission medium that changes over time, wherein the EM wave is emitted at discrete frequencies corresponding to known absorption frequencies of known transmission mediums; receiving, by a receiver of the electronic device, a reflected EM wave reflected off at least one object in the environment; determining, by the one or more processors of the electronic device, a spectral response of a received signal indicative of the reflected EM wave, the spectral response including absorption spectra at a frequency in the THz frequency band that is indicative of the transmission medium in the environment; comparing, by the one or more processors, the absorption spectra with known absorption spectra of target transmission mediums; identifying, by the one or more processors and based on results of the comparing, a particular target transmission medium as being the transmission medium in the environment; and determining, by the one or more processors, a concentration level of the particular target transmission medium in the environment.

One or more of the disclosed embodiments provide one or more of the following advantages. The disclosed THz spectroscopy and imaging systems and methods for estimating concentration levels of chemicals or the quality of a transmission medium (e.g., gas, liquid, solid or plasma materials) in a dynamic environment using an electronic device (e.g., a smart phone, tablet computer, wearable computer). With THz spectroscopy and imaging: 1) there is no need for an aperture on the consumer electronic device; 2) gas, liquid and solid materials can be detected; 3) there is very low idle-time current consumption because there are no material properties of a sensor to support; 4) there is no drift over time because a pure electromagnetic wave is used for detection; and 5) imaging applications for health monitoring (e.g., detecting skin cancer) can be realized on consumer electronic devices.

The details of one or more implementations of the subject matter are set forth in the accompanying drawings and the description below. Other features, aspects and advantages of the subject matter will become apparent from the description, the drawings and the claims.

BRIEF DESCRIPTION OF THE DRAWINGS

FIG. 3 is a table describing environment and system losses, their contributing factors and their effects on the spectral response of the received signal, according to an embodiment.

FIGS. 7A and 7B illustrate spectral responses of a received signal before and after compensation to restore the absorption signature peak below a noise floor of the baseband receiver, according to an embodiment.

FIG. 18 is a flow diagram of THz spectroscopy process in a dynamic environment, according to an embodiment.

FIGS. 19A and 19B is a flow diagram of a process of removing impairments from a spectral response of a received signal due to environmental and system losses.

FIG. 27 is plot of transmit signal power versus number of antenna elements, according to an embodiment.

DETAILED DESCRIPTION

Figure 1A:
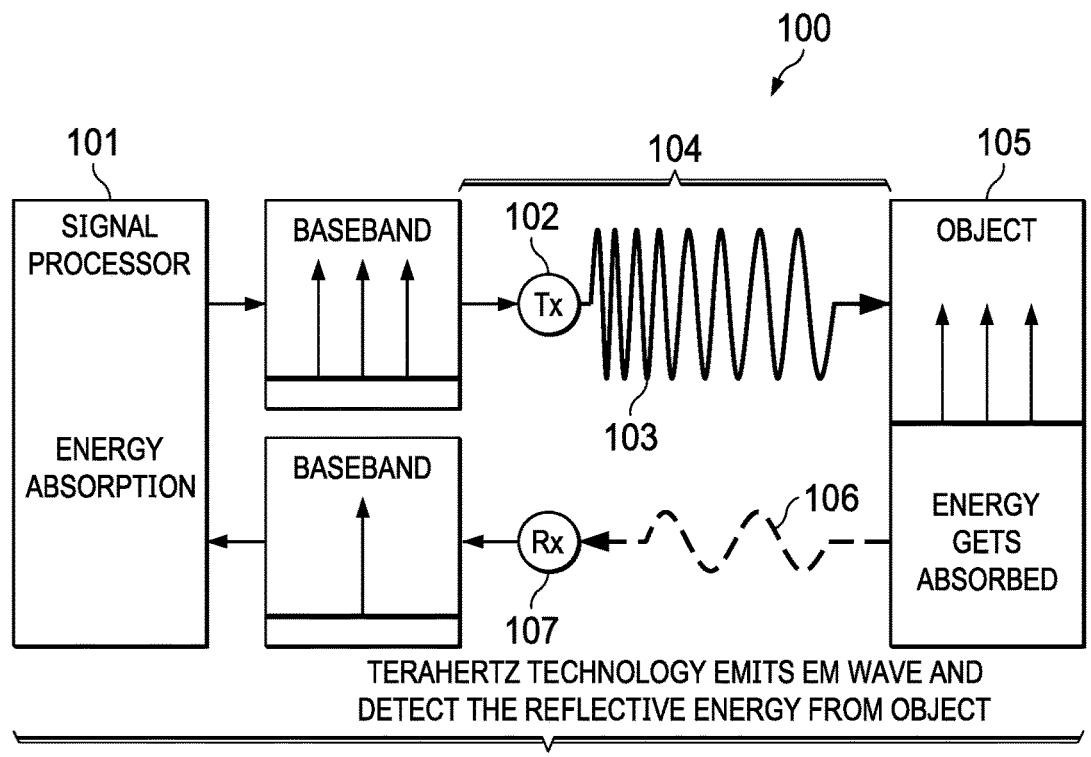
FIG. 1A is a conceptual block diagram of a THz spectroscopy system for estimating the concentration levels of chemicals or quality of a transmission medium or ambience in a dynamic environment, according to an embodiment.

A molecule can absorb and re-emit an electromagnetic (EM) wave at certain frequencies, specific to the energy transitions of either electronic, vibrational, or rotational modes. Each molecular species absorbs the EM wave in a unique spectral pattern. In the gas phase, for example, the rotational transition modes occur in polar molecules that span from the microwave to infrared (IR) spectra. The rotational transitions result in an absorption spectrum that contains Lorentzian resonances at discrete frequencies. The absorption spectrum is unique to the molecule. This uniqueness enables the classification and recognition of polar gases via THz spectroscopy.

Disclosed is a THz spectroscopy and imaging system and method whereby EM waves are emitted in a dynamic environment in real-time by a transmitter of an electronic device in the THz frequency band. The EM waves are reflected by objects (e.g., walls) in the dynamic environment and received by a receiver of the electronic device in real-time. If a transmission medium (e.g., gas, liquid, solid, plasma) with an absorption frequency in the THz frequency band is present between the transmitter and the reflective object, the received signal level at that frequency will be lower than those at other frequencies. Thus, transmission mediums in the dynamic environment can be detected by illuminating one or more reflective objects in the dynamic environment with a range of THz frequencies covering the absorption spectra of the transmission mediums to be detected and observing the reflected spectrums.

In an embodiment, measured absorption spectra are compared to known absorption spectra of target transmission mediums by computing a distance metric (e.g., Euclidian distance) between the measured and known absorption spectra. The target transmission medium having an absorption spectra that is a minimum distance from the measured absorption spectra based on the distance metric is an identified transmission medium in the dynamic environment. After identifying the target transmission medium, a reference library is used to estimate the concentration level of the target transmission medium in the dynamic environment based on the measured absorption level and a computed total path length of the received signal in the dynamic environment. In a dynamic environment, the total path length of the reflected THz signal changes due to scattering and multiple reflections off objects with different angles of incidence. The concentration level in parts per million (PPM) will differ due to different path lengths. In an embodiment, the total path length of a THz signal is determined using time of arrival (TOA) calculations.

Embodiments are also disclosed for compensating the spectral response of the received signal to remove fixed and frequency-specific losses in the spectral response due to the environment and THz spectroscopy system limitations. Compensation for these losses include using a known reference absorption spectra for a common transmission medium (e.g., $O_2$, N, $H_2$), and subtracting a delta between the measured and known absorption spectra. A fixed loss due to frequency range error is estimated by determining a frequency in the THz frequency band with minimum loss, and extrapolating the signal strength at that frequency across the entire THz spectrum. The fixed loss is the difference between the transmitted signal strength and the extrapolated signal strength. After the fixed loss is determined, the fixed loss is subtracted from the spectral response of the received signal.

Multipath reflections off objects with different reflection angles can impair the signal-to-noise ratio (SNR) of the received signal. In an embodiment, a hardware architecture includes a dual receiver antenna circuit and power combiner to improve the SNR of the received signal using multiple polarizations for the transmitted and received THz signals.

In an embodiment, motion sensors (e.g., accelerometers, gyros) are used to adjust the duty cycle of THz wave scanning to improve battery performance, and ambient sensors (e.g., pressure sensor, temperature sensor, humidity sensor) are used to reduce the impact of environmental factors (e.g., change in humidity or atmospheric pressure) on detection accuracy. Additionally, localization techniques (e.g., cellular, satellite-based, WiFi) can be used to account for different country regulations/standards regarding safe or legal concentration levels of chemicals or quality of a transmission medium. In an embodiment, the THz system uses a "sniff" mode of operation that causes THz waves to be emitted at discrete frequencies of known target gases using a bias-controlled varactor circuit.

Example THz Spectroscopy System

FIG. 1A is a conceptual block diagram of a THz spectroscopy system 100 for estimating the concentration levels of chemicals or quality of a transmission medium or ambience in a dynamic environment, according to an embodiment. System 100 enables consumer electronic devices (e.g., smartphones, tablet computers, wearable devices) to perform spectroscopy applications using EM waves in the THz frequency band.

The term "dynamic environment" as used in the specification is an environment where the transmission medium for the THz EM waves continuously changes in concentration level, and/or the location and/or orientation of the electronic device transmitting/receiving the THz EM waves is changing, and/or the location and/or orientation of one or more objects reflecting the THz waves in the environment are moving. An example of a dynamic environment is an indoor location (e.g., a room in a house or office in a building) where concentration levels of dangerous gases (e.g., CO, $CO_2$) are continuously changing.

The term "transmission medium" as used in the specification and claims is any material substance (e.g., solid, liquid, gas or plasma) that can propagate THz EM waves. The term "baseband transceiver" as used in the specification and claims is intended to include any chip, chip set or system on chip (SoC) that transmits and receives baseband signals in the THz frequency band of about 0.3 THz to about 18 THz.

System 100 includes signal processor 101, baseband transmitter 102, baseband receiver 107 and reflective object 105 (e.g., a wall, ceiling, floor). Signal processor 101 commands baseband THz transmitter 102 to emit into dynamic environment 104 a continuous wave (CW) tone across the THz frequency band (hereinafter, referred to as "transmitted signal 103 (Tx)"). In an embodiment, transmitted signal 103 can be a pulsed waveform. Transmitted signal 103 reflects off object 105 and the reflected energy is received by THz baseband receiver 107 (hereinafter, referred to as "received signal 106").

In an embodiment, baseband transmitter 102 and baseband receiver 107 are implemented as separate integrated circuit (IC) chips or are combined into a single IC chip referred to as a THz transceiver. In an alternative embodiment, baseband receiver 107 is implemented in single receiver or dual receiver configuration for multiple polarizations, as described in reference to FIG. 11. In an embodiment, signal processor 101, baseband transmitter 102 and baseband receiver 107 are included together in a single housing of an electronic device, such as a smartphone, tablet computer or wearable device (e.g., a smartwatch), as described in reference to FIG. 17.

Figure 1B:
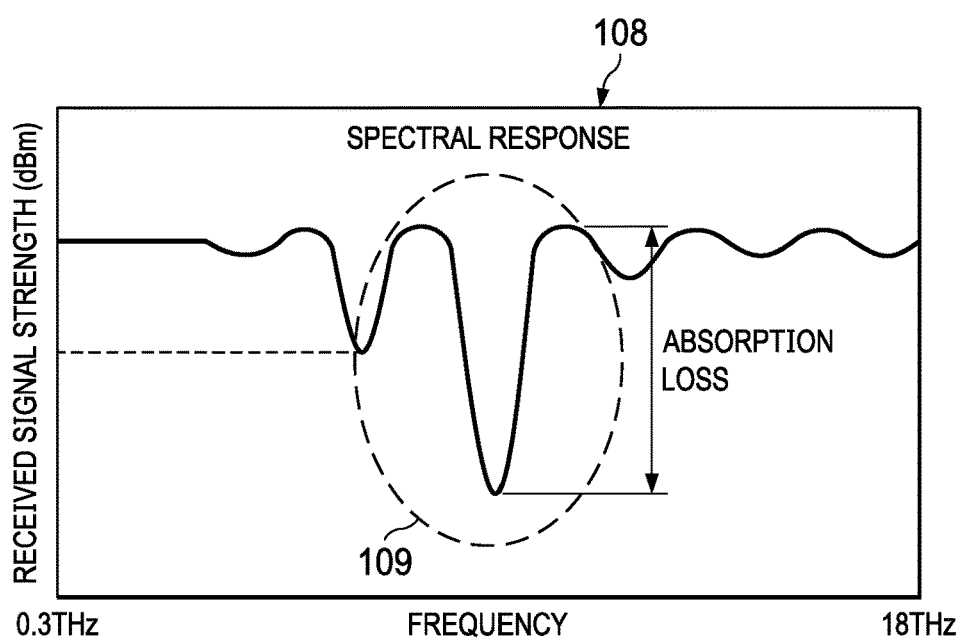
FIG. 1B illustrates an example spectral response of a received signal, according to an embodiment.

FIG. 1B illustrates spectral response 108 of received signal 106 computed by signal processor 101. The vertical axis of the plot is received signal strength (dBm) and the horizontal axis of the plot is frequency (THz). As can be observed from FIG. 1B, spectral response 108 includes a unique absorption signature 109 at a specific frequency in the THz frequency band. Signal processor 101 compares absorption signature 109 to known absorption signatures for various target transmission mediums. If absorption signature 109 matches a known absorption signature for a target transmission medium, the target transmission medium is identified as being present in dynamic environment 104. The concentration level for the identified transmission medium is then estimated using a reference library of known concentration levels for the target transmission medium based on the measured absorption loss and path length of the received signal. In an embodiment, the reference library can be implemented as a table, as described in reference to FIG. 16.

Figure 2A:
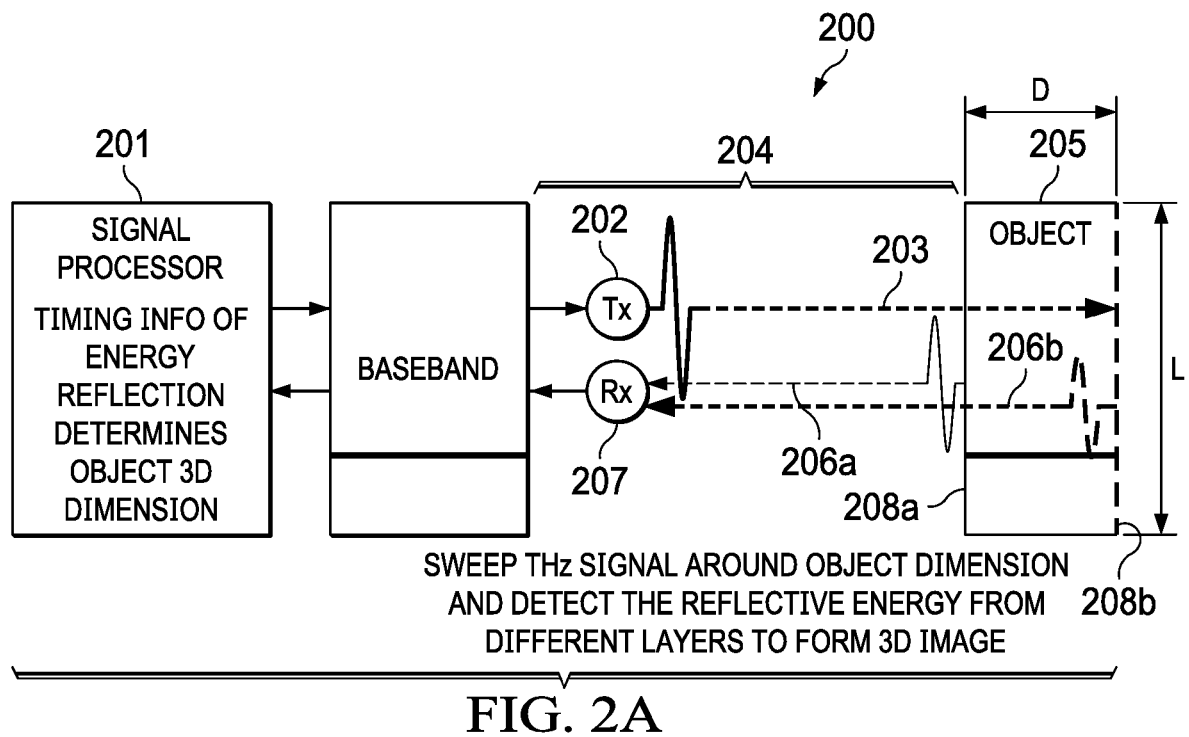
FIG. 2A is a conceptual block diagram of a THz imaging system, according to an embodiment.

FIG. 2A is a block diagram illustrating a THz imaging system 200, according to an embodiment. System 200 includes signal processor 201, baseband transmitter 202, baseband receiver 207 and reflective object 205. System 200 enables consumer electronic devices to perform imaging applications using THz EM waves.

In the example shown, signal processor 201 commands baseband THz transmitter 202 to emit into dynamic environment 204 a continuous wave (CW) tone across the THz frequency band (hereinafter, referred to as "transmitted signal 203 (Tx)"). In an embodiment, transmitted signal 203 can be a pulsed waveform. Transmitted signal 203 reflects off object 205 in environment 204 and the reflected energy is received by THz receiver 207 (hereinafter, referred to as "received signal 206"). In an embodiment, baseband transmitter 202 sweeps transmitted signal 203 around a dimension L of object 205.

Figure 2B:
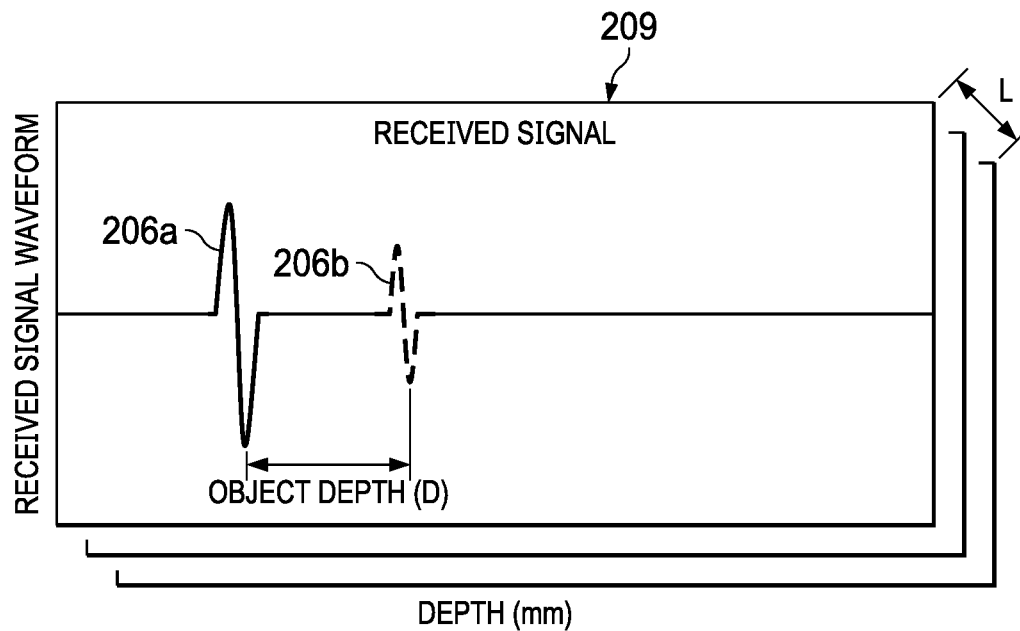
FIG. 2B illustrates received signal waveforms resulting from a sweeping transmitted signal around an object dimension, according to an embodiment.

Object 205 can have any number of layers. An example multilayer object 205 is human skin. In the example shown, object 205 has two layers 208a, 208b. Baseband receiver 207 obtains received signals 206a, 206b at different time instances. Signal processor 201 estimates the TOA of each of received signals 206a, 206b, by computing the difference between a start time of transmission of transmitted signal 203 and start times for receipt of received signals 206a, 206b. FIG. 2B illustrates received signal strength waveforms 206a, 206b as a function of depth (mm) swept over dimension L of reflective object 205. The determination of the depth D between layers 208a, 208b of reflective object 205 is determined based on the TOA calculations.

FIG. 3 is a table 300 describing environment and system losses, their contributing factors and their effects on the spectral response of a received signal, according to an embodiment. As described above in reference to FIGS. 1A, 1B, THz spectroscopy attempts to match an absorption signature at particular frequency in the THz frequency band with a known target absorption signature of a target transmission medium. In a dynamic environment (e.g., where gas concentration levels continuously change), the received signals are impaired due to environment and system losses, as described in the table of FIG. 3. The losses vary as a function of frequency and transmission medium. Accordingly, to operate effectively in a dynamic environment, there is a need to estimate and compensate for environmental and system losses.

For environmental losses, contributing factors include but are not limited to: the distance between the sensor and the reflective object, atmospheric absorption loss, angle of incidence at the reflective object and the nature of the reflective object (e.g., the refractive index). The effect of the environment loss on THz spectroscopy system 100 is a lowering of the SNR at the receiver. For example, reflective energy is a function of distance. As distance increases, received signal strength decreases. Additionally, THz EM waves are absorbed in the atmosphere as they propagate. The longer the path length, the more absorption loss. Depending on a certain angle at which the transmitted signal hits the reflective object (i.e., the angle of incidence), the received signal strength may degrade as compared to other angles of incidence. Finally, some common materials like plywood, pine wood and brick, have lower refractive indexes which leads to higher reflective loss. For system errors, the contributing factors include but are not limited to losses due to frequency band. The primary effect on the THZ spectroscopy system 100 due to system losses is an inaccurate concentration level estimation at high frequencies.

Figure 4:
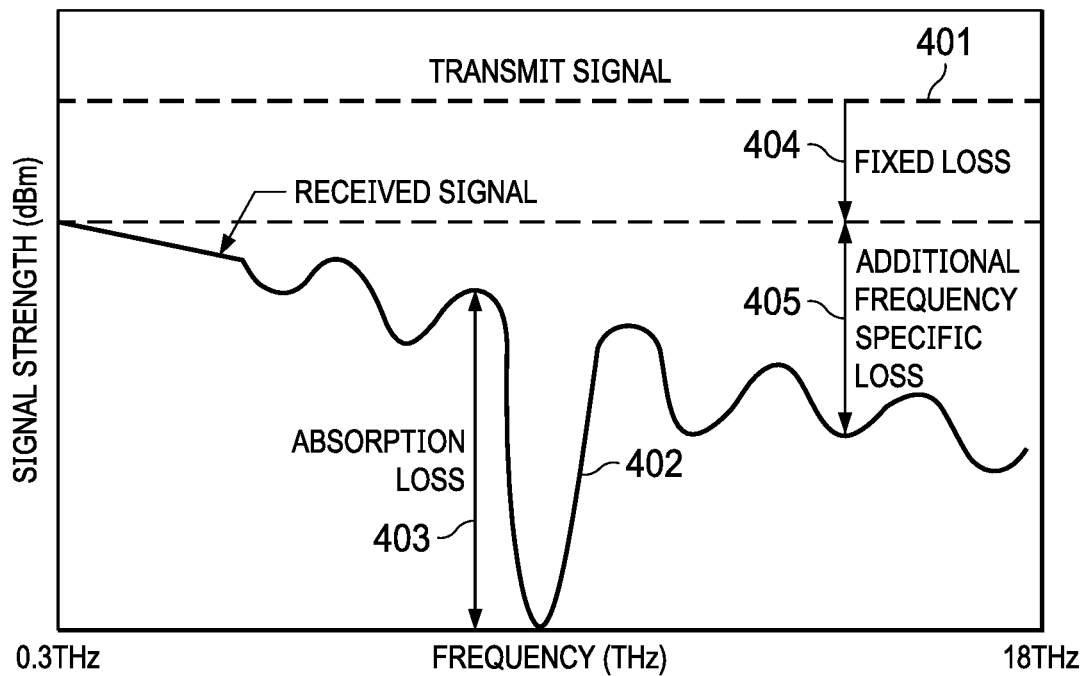
FIG. 4 illustrates the spectral response of a received signal, including absorption loss that varies as a function of frequency and transmission medium, according to an embodiment.

FIG. 4 illustrates an example spectral response 400 of a received signal, including losses that vary as a function of frequency and transmission medium, according to an embodiment. Transmitted signal 401 is shown having a constant transmission energy. Received signal 402 is shown as having absorption signature 403 at a particular frequency in the THz frequency band. Also, shown is the fixed loss 404 and additional frequency-specific loss 405 in received signal strength due to environmental and system losses, respectively. Techniques for estimating and compensating for environmental and system losses are described in reference to FIGS. 5A-5C.

Figure 5A:
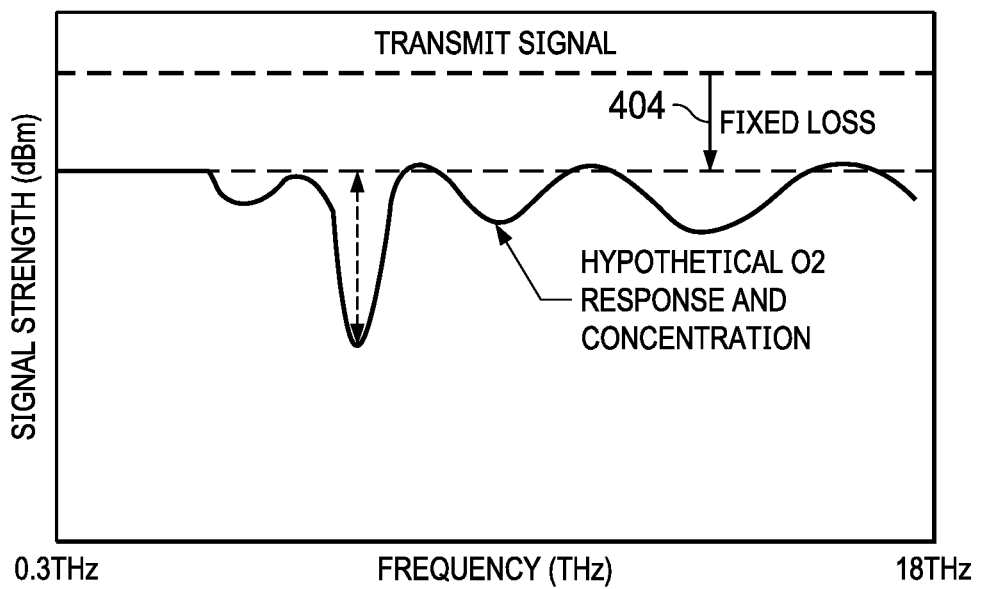
FIG. 5A illustrates a hypothetical spectral response of Oxygen ($O_2$), Nitrogen (N) or other known atmospheric gas concentration, according to an embodiment.
Figure 5B:
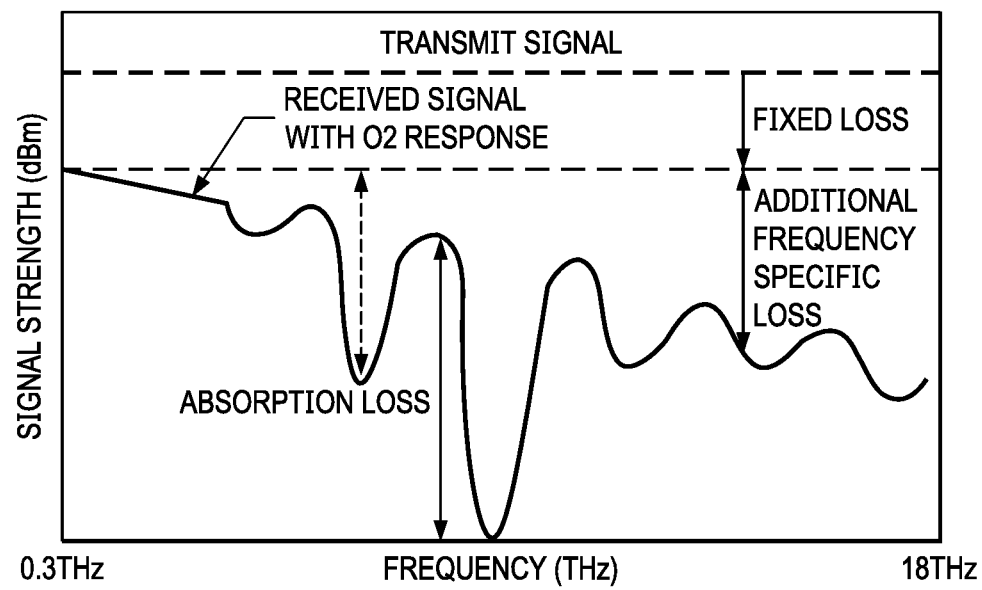
FIG. 5B illustrates a spectral response of a received signal with the hypothetical spectral response of Oxygen ($O_2$), Nitrogen (N) or other known atmospheric gas concentration shown in FIG. 5A, according to an embodiment.
Figure 5C:
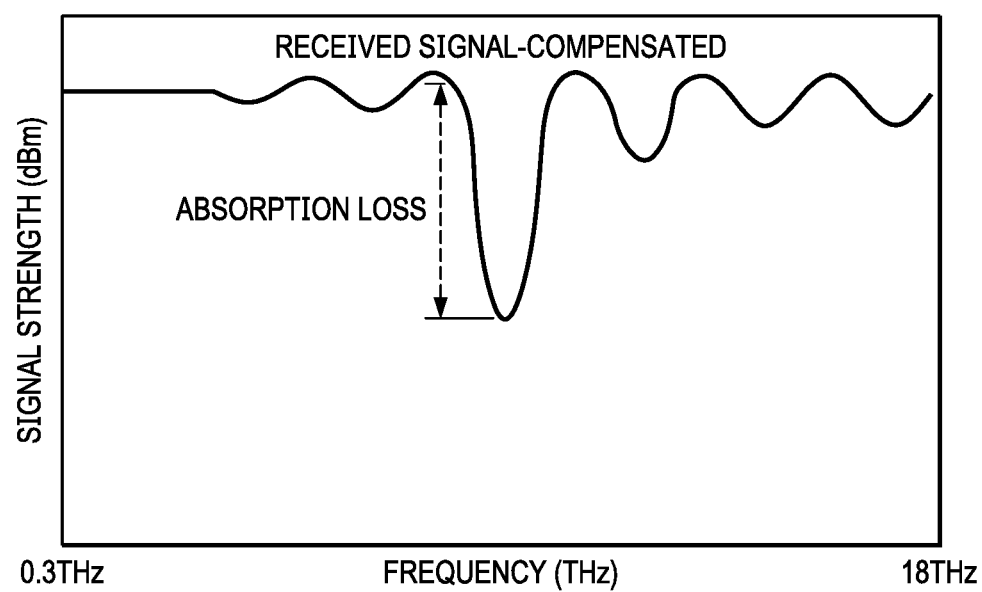
FIG. 5C illustrates a spectral response of the received signal compensated for frequency-specific loss using the hypothetical spectral response of Oxygen ($O_2$), Nitrogen (N) or other known atmospheric gas concentration shown in FIG. 5A, according to an embodiment.

FIG. 5A illustrates a hypothetical spectral response 500 of Oxygen ($O_2$), Nitrogen (N) or other known atmospheric gas concentration, according to an embodiment. In an embodiment, the known spectral response of a transmission medium such as $O_2$ is used to remove the impairments in the spectral response of a received signal due to the environment. Other known hypothetical spectral responses can also be used, such as the spectral response for Nitrogen (N) or hydrogen ($H_2$). FIG. 5B illustrates spectral response 501 of a received signal with spectral response 500 of $O_2$ shown in FIG. 5A. FIG. 5C illustrates spectral response 502 of the received signal compensated for environmental loss using spectral response 500, according to an embodiment. The frequency-specific loss due to the environment is compensated by subtracting spectral response 500 of $O_2$ from the spectral response of the received signal.

Figure 6A:
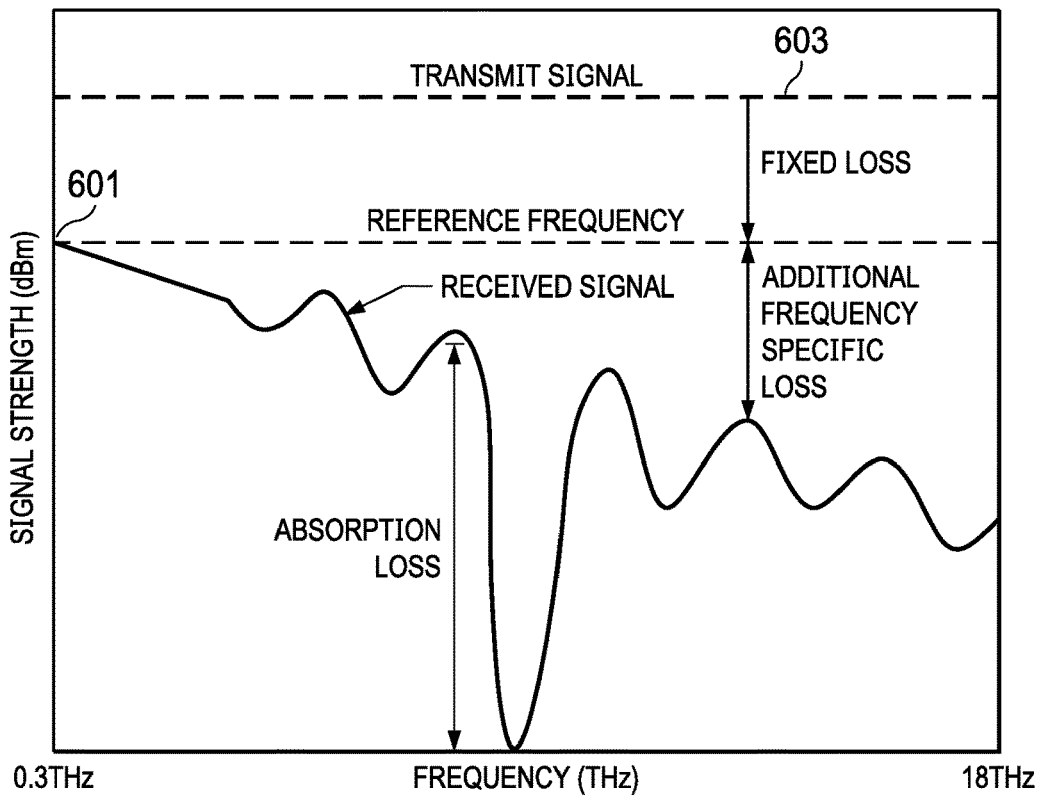
FIGS. 6A and 6B illustrate spectral responses of a received signal before and after compensation for fixed and additional frequency-specific impairments, according to an embodiment.
Figure 6B:
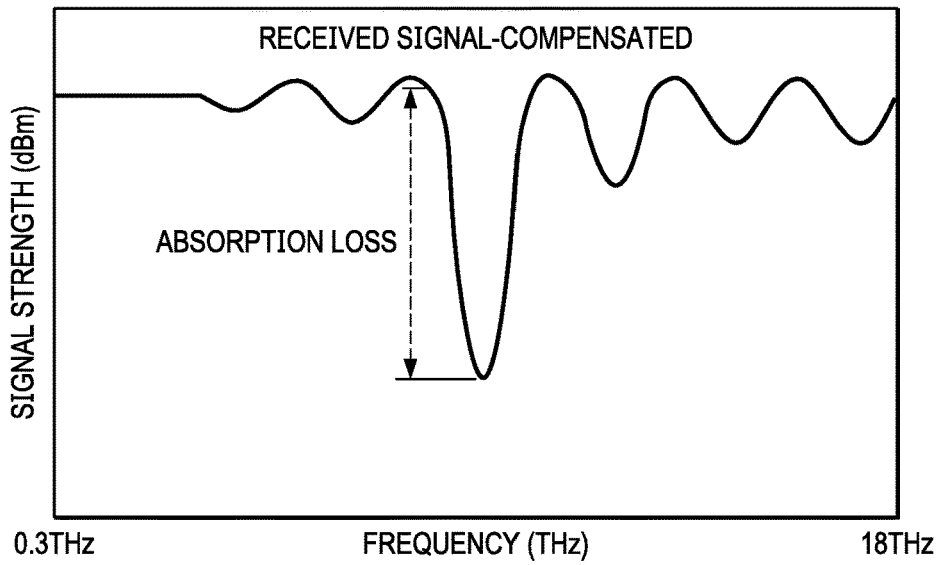

FIGS. 6A and 6B illustrate spectral responses 600, 602 of a received signal before and after compensation for fixed and additional frequency-specific losses, according to an embodiment. In this technique, reference frequency 601 is selected in the THz frequency band at which environment loss is minimal across the THz frequency band. The signal strength at reference frequency 601 is extrapolated across the entire THz frequency band. The difference between the signal strength of the transmitted signal 603 and the extrapolated received signal strength associated with reference frequency 601 is the fixed loss of the system to be compensated. The additional frequency-specific loss shown in FIG. 6A is determined based on the trend line of the received signal strengths of other peaks (e.g., average of peaks) in the spectral response of the received signal at other frequencies. Any peak that is small or negligible is ignored.

The spectral response of the received signal is compensated by subtracting the signal strengths associated with the fixed loss and additional frequency-specific loss from the spectral response of the received signal, as shown in FIG. 6B.

FIGS. 7A and 7B illustrate compensated and uncompensated spectral responses 700, 702 of a received signal for restoring a portion of the absorption signature peak below a noise floor of the baseband receiver, according to an embodiment. THz spectroscopy requires that the spectral response of the received signal be matched with a known spectral response of a target transmission medium. In some cases, the spectral response 700 of the received signal is impaired by environment/system losses that vary as a function of frequency and transmission medium. When the losses are high, the absorption signature peak can fall below noise floor 701 of the baseband receiver, as shown in FIG. 7A, which means its shape and size is unknown. FIG. 7B illustrates a compensated spectral response 702 having a truncated and therefore inaccurate measured absorption loss. The absorption signature peak below noise floor 701 can be restored, however, by curve fitting, as described in reference to FIG. 8.

Figure 8:
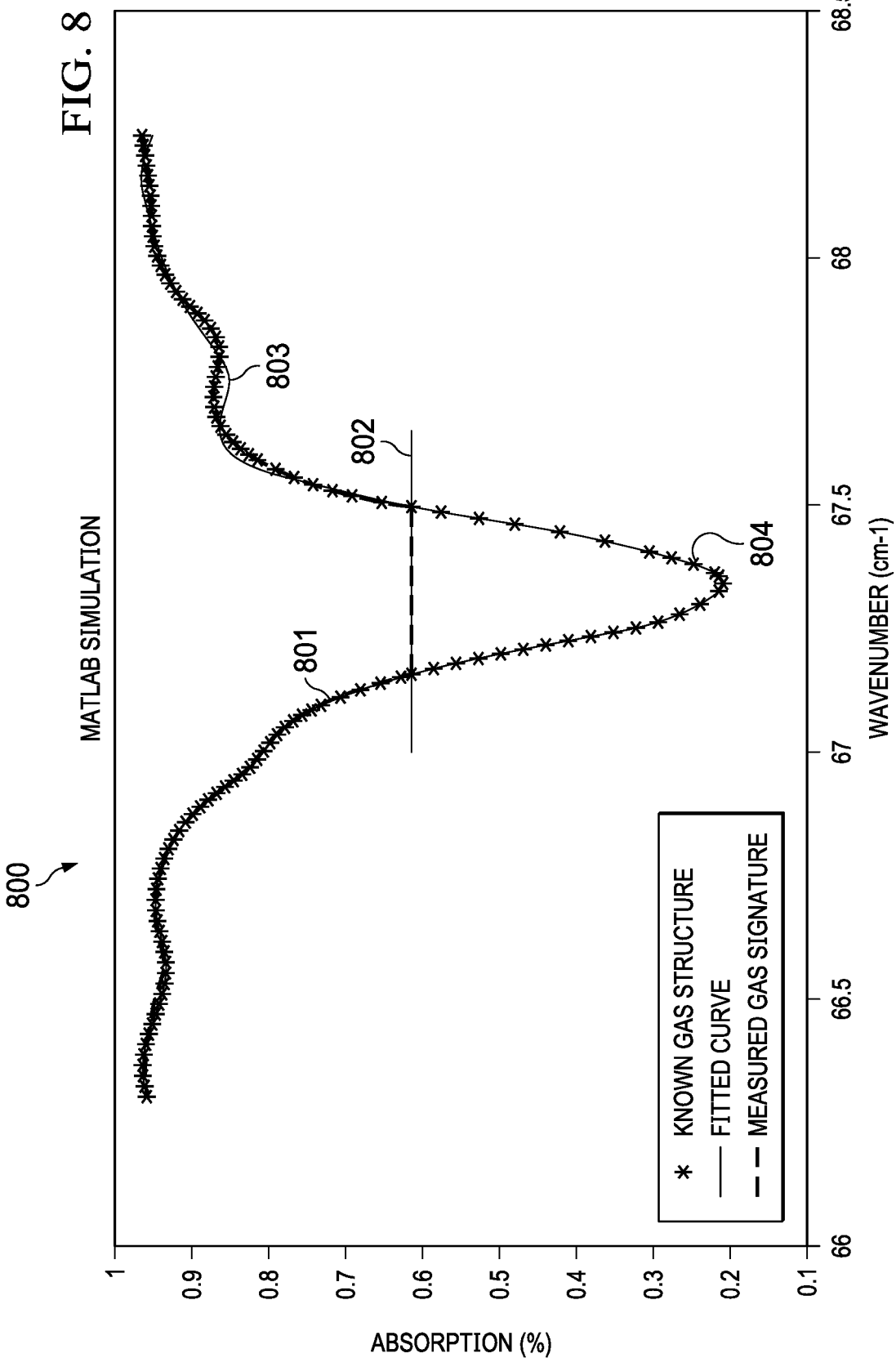
FIG. 8 is a plot of a simulated absorption signature where the peak of the signature is restored using curve fitting, according to an embodiment.

FIG. 8 is a plot of a simulated absorption signature where the peak of the signature is restored using curve fitting, according to an embodiment. Since the absorption signature is unique for a given transmission medium, a curve fitting technique (e.g., Sum of Sines) is used to estimate the peak below receiver noise floor 802, as shown in FIG. 8. Any suitable curve fitting technique can be used to restore the peak of the absorption loss signature. In the example shown, known absorption signature data 804 for a gas is used with measured absorption signature data 801 in the Sum of Sines curve fitting algorithm to fit curve 803 to known absorption signature data 804 below noise floor 802.

Figure 9:
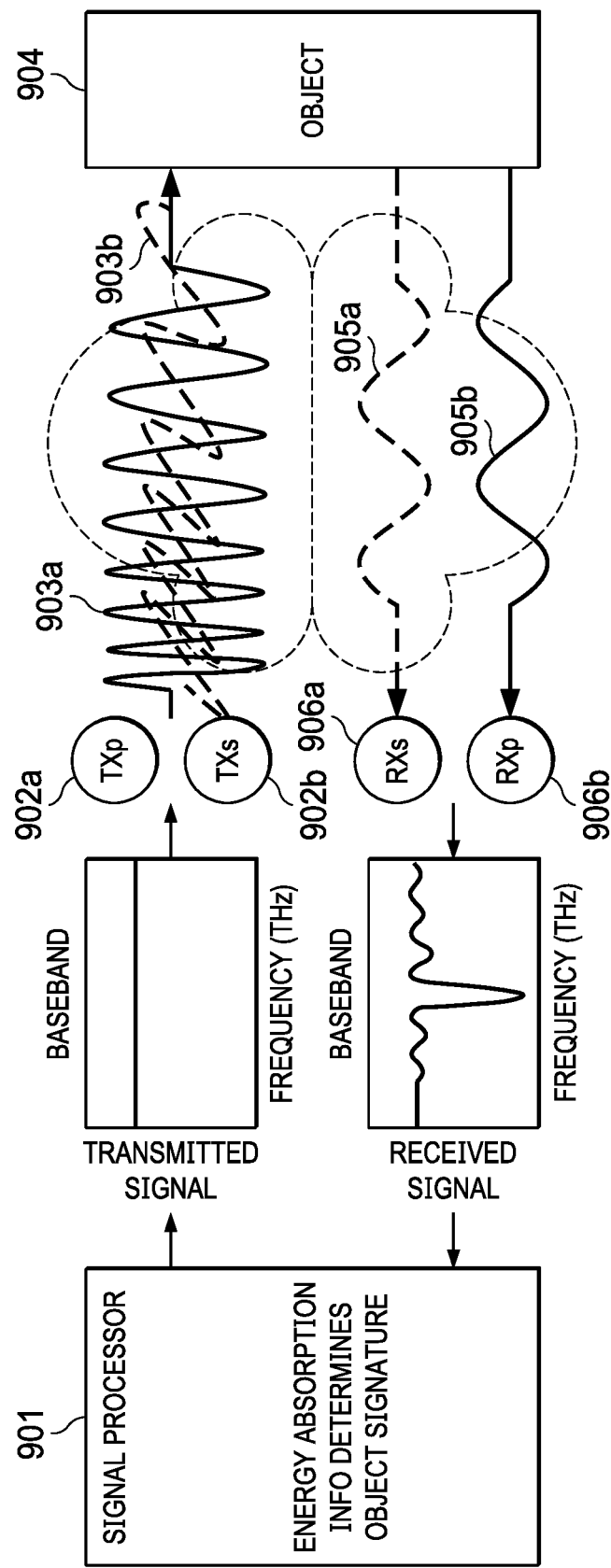
FIG. 9 is a block diagram illustrating transmitted and received signals with multiple polarizations, according to an embodiment.

FIG. 9 is a block diagram illustrating transmitted and received signals for spectroscopy and imaging with multiple polarization, according to an embodiment. Polarization is a property that applies to transverse waves that specifies geometrical orientation of the oscillations. For example, in a transverse wave, the direction of the oscillation is perpendicular to the direction of motion of the wave. For a given polarization, if the angle of incidence is large it can result in significant signal loss. The angle of incidence is the angle between a ray incident on a surface and a line perpendicular to the surface at the point of incidence.

A solution to improve signal quality is to use one or more antenna diversity techniques, including but not limited to: spatial diversity that uses multiple antennas with the same characteristics that are physically separated from one another, pattern diversity that uses two or more co-located directional antennas with different radiation patterns, transmit/receive diversity that uses two separate, co-located antennas for transmit and receive functions, adaptive arrays (e.g., a single antenna with active elements or an array of similar antennas with the ability to change their combined radiation pattern) and polarization diversity that combines pairs of antennas with orthogonal polarizations (e.g., horizontal/vertical, +/− slant 45°, Left-hand/Right-hand circular polarizations, etc.).

In the example THz spectroscopy and imaging system 900 shown in FIG. 9, polarization diversity is used to improve the SNR of the received signal. Signal processor 901 commands baseband transmitters 902a, 902b to emit multiple transmitted signals 903a, 903b with different polarizations (e.g., vertical and horizontal polarization) to ensure baseband receivers 906a, 906b receive received signals 905a, 905b with different polarizations regardless of the angle of incidence of impingement on object 904. Note that the SNR of received signals 905a, 905b is improved by combining received signals 905a, 905b with the different polarizations in baseband receivers 906a, 906b. Note that the polarized THz signals can be emitted and received in parallel with two transmitters and two receivers or emitted and received by a single transmitter and receiver by time multiplexing the polarized THz signals.

Figure 10:
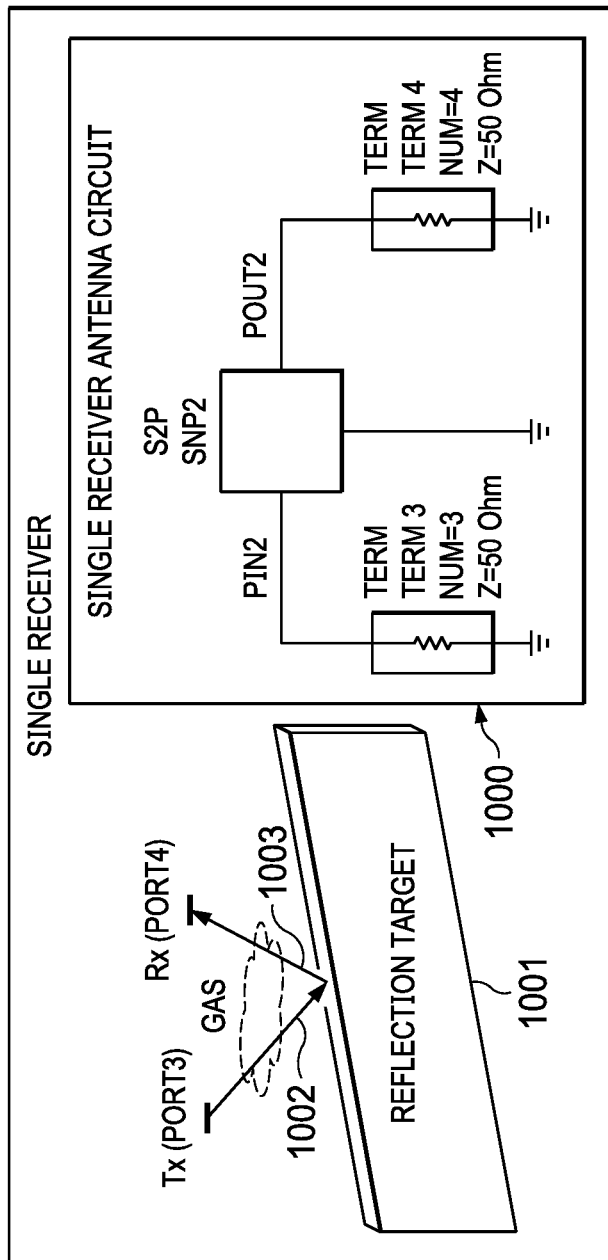
FIG. 10 is a schematic diagram of a single receiver antenna circuit for in-plane transmission/reception of transmitted and received THz signals, according to an embodiment.

FIG. 10 is an Advanced Design System (ADS) schematic diagram of a single transceiver antenna circuit model 1000 for simulation of in-plane transmission/reception of transmitted and received signals, respectively, according to an embodiment. The component SNP2 shown in circuit model 1000 is a two-port antenna component that imports a touchstone file, and the two 50 Ohm resistors are used for tuning the SNP2 component. As shown, a first port (port 3) of the transceiver emits a THz wave which impinges reflection target 1001 at an angle of incidence 1002, resulting in a reflection signal leaving the impinged surface at a reflection angle 1002. The reflected signal is received at a second port (port 4) of the transceiver. Circuit 1000 suffers from impaired SNR due to the angle of incidence 1002.

Figure 11:
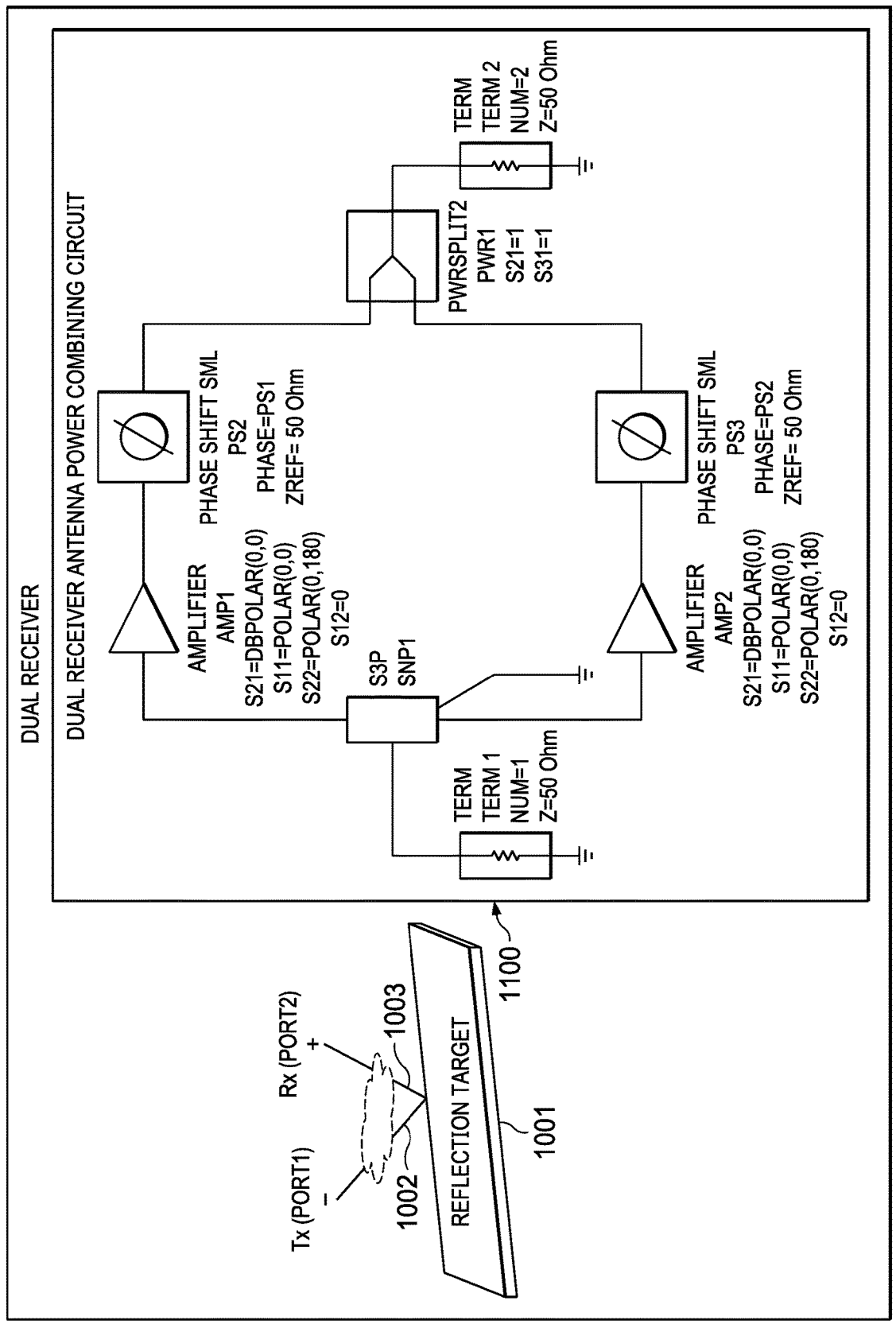
FIG. 11 is a schematic diagram of a dual receiver antenna and power combining circuit for transmission/reception THz signals using multiple polarizations, according to an embodiment.

FIG. 11 is an ADS schematic diagram of a dual receiver antenna and power combining circuit model 1100 for simulating transmission/reception of transmitted and received signals using multiple polarizations, according to an embodiment. Circuit model 1100 includes two-port antenna component SNP1, amplifier components AWP1, AMP2, phase shifter components PS2, PS3 and power combiner PWR1. The two 50 Ohm resistors are used for tuning the SNP2 component. As shown, a first port (port 1) of the transceiver emits a THz wave which impinges reflection target 1001 at an angle of incidence 1002, resulting in a reflection signal leaving the impinged surface at a reflection angle 1002. The reflected signal is received at a second port (port 2) of the transceiver. Circuit 1100 provides multiple polarizations to improve SNR.

Figure 12:
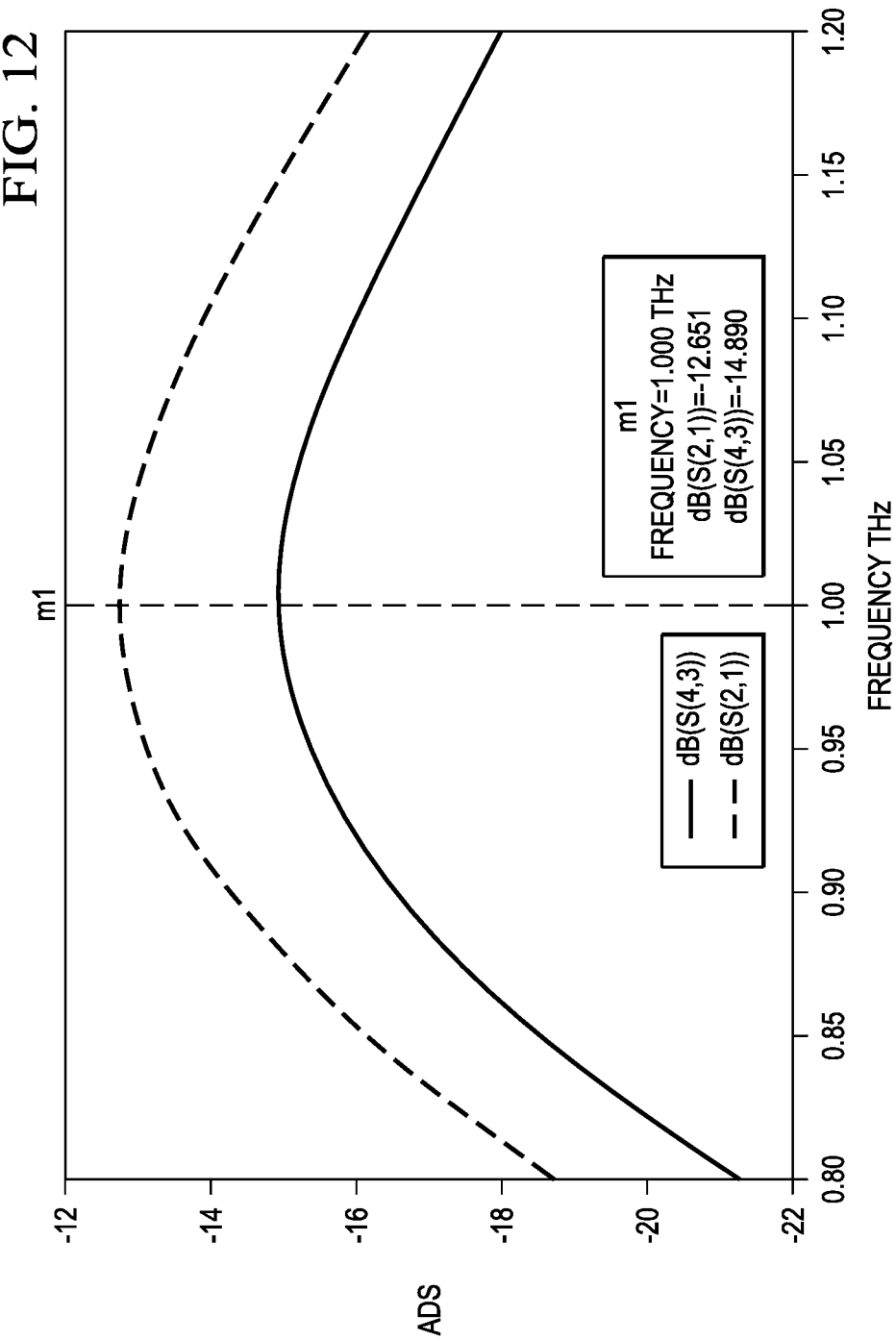
FIG. 12 is a plot illustrating the increased power transfer gain for a 45° reflection angle using the dual receiver antenna and power combining circuit of FIG. 11, according to an embodiment.

The two circuit models 1000, 1100 described above were simulated using High Frequency Structure Simulator (HFSS) developed by ANSYS® Inc. with reflection angles 1002a of 45° and −45° and a sweep frequency of 1 THz. FIG. 12 shows the simulation results for the 45° reflection angle. As can be observed from FIG. 12, dual receiver antenna circuit model 1100 with cross polarization achieves gains in power transfer of ~3 dB over single receiver antenna circuit model 1000 with no cross polarization.

Figure 13:
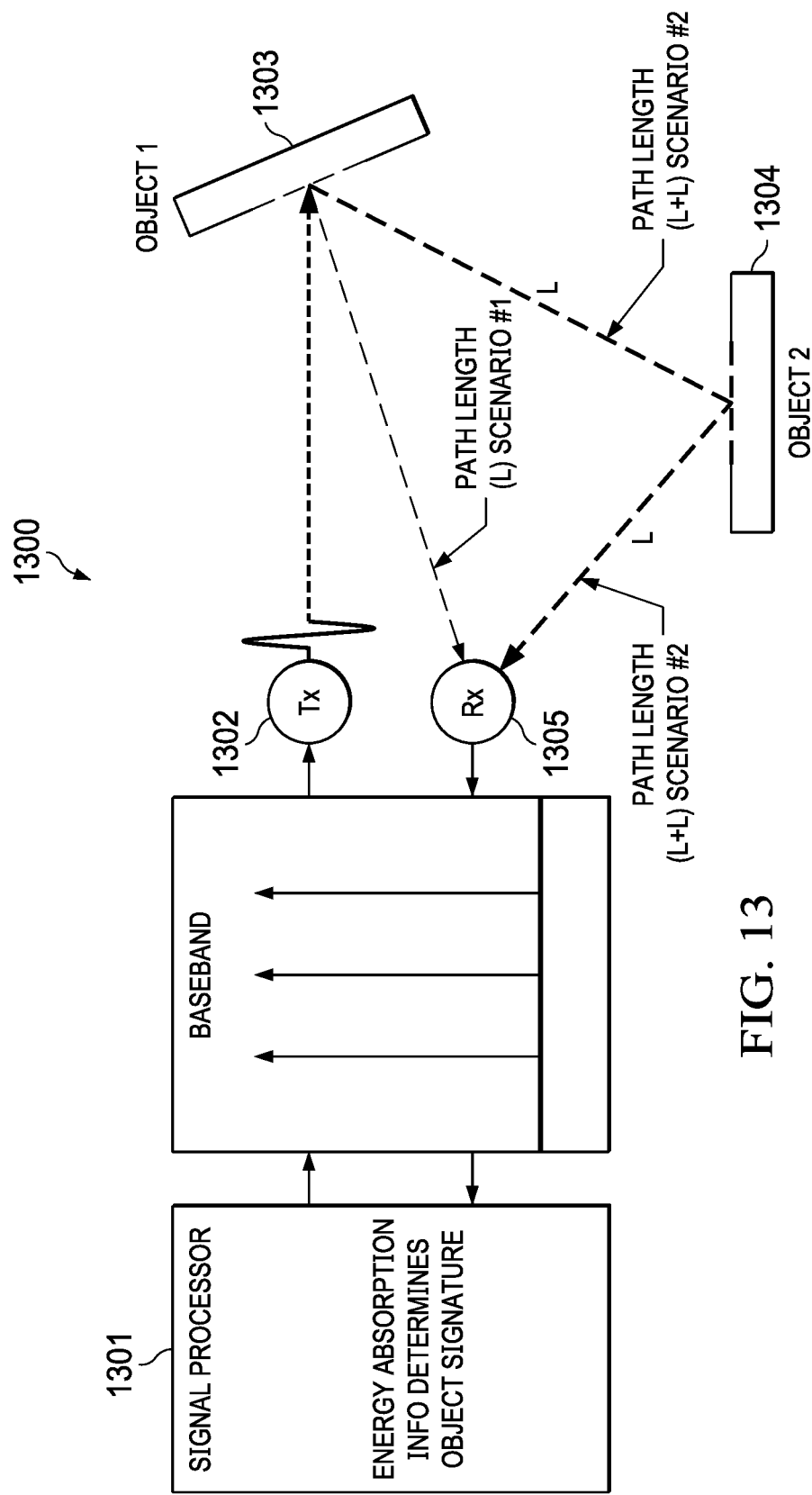
FIG. 13 is a block diagram illustrating an increase in path length of a received THz signal due to multiple reflection surfaces in the dynamic environment, according to an embodiment.

FIG. 13 is a block diagram illustrating an increase in path length of a received signal (for imaging or spectroscopy use cases), according to an embodiment. Path length is the total distance traveled by the THz signal in free-space before it arrives at baseband receiver 1305. For a given transmission medium, absorption frequency path length determines the absorption loss. The longer the path length, the more absorption loss that is incurred. In a dynamic environment, path length changes due to multiple reflections off object surfaces at different angles of incidence.

In a first example scenario, signal processor 1301 commands baseband transmitter 1302 to emit a transmitted THz signal, which is reflected off first object 1303 in the dynamic environment and travels a first path length L to baseband receiver 1305. In a second scenario, the transmitted signal is reflected off first object 1303, travels a second path length L, reflects off second object 1304 and travels a third path length L to baseband receiver 1305 for a total path length of 2 L. Note that in this example each path length is L. In a practical system, there can be any number of reflective objects and path lengths and the path lengths can be the same or different.

Figures 14, 16:
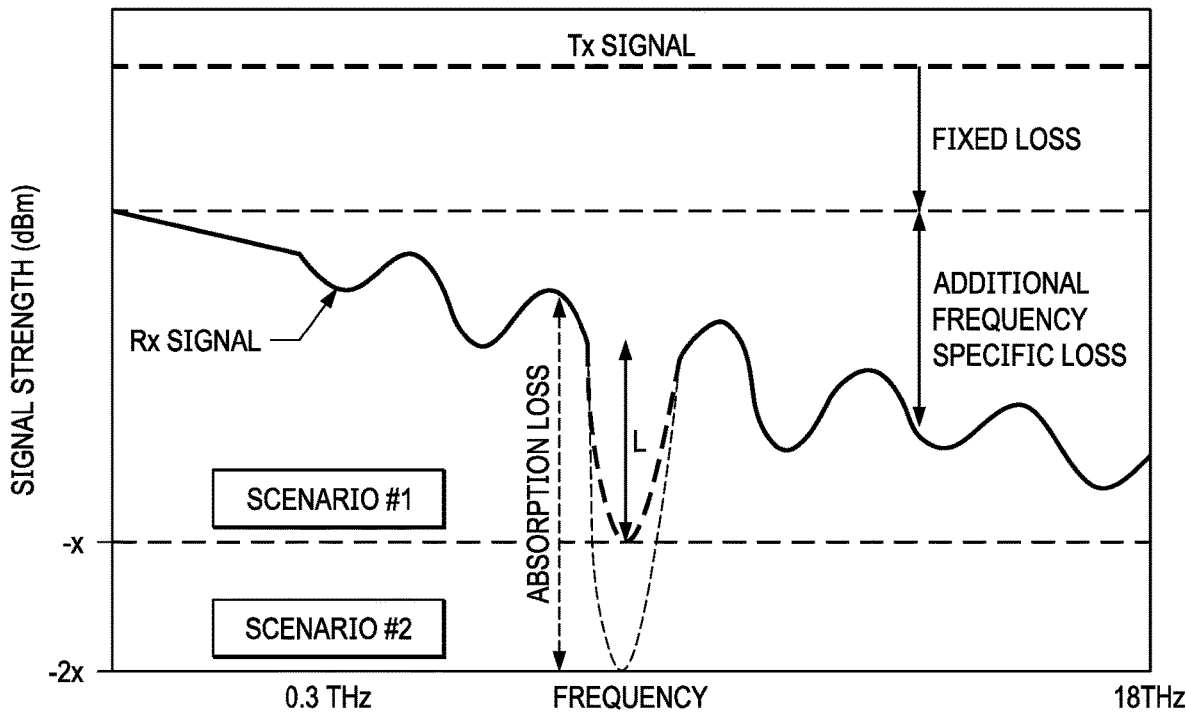
FIG. 14 is a plot of a spectral response of the received signal due to the change in the path length shown in FIG. 13, according to an embodiment.
FIG. 16 is an example table of the reference library, according to an embodiment.

FIG. 14 is a plot of a spectral response of the received THz signal due to the change in the path length shown in FIG. 13, according to an embodiment. As can be observed in FIG. 14, in the first scenario the received signal absorption loss is −x dBm for a path length L in signal strength and in the second scenario the received signal absorption loss is −2x dBm for a path length of 2 L, or twice the absorption path loss. Based on the two scenarios, the concentration level in parts per million (PPM) of the transmission medium differs due to the different path lengths. To address the change in concentration level as a function of path length, concentration level is estimated using an empirically generated reference library, as described in reference to FIGS. 15 and 16.

Figure 15:
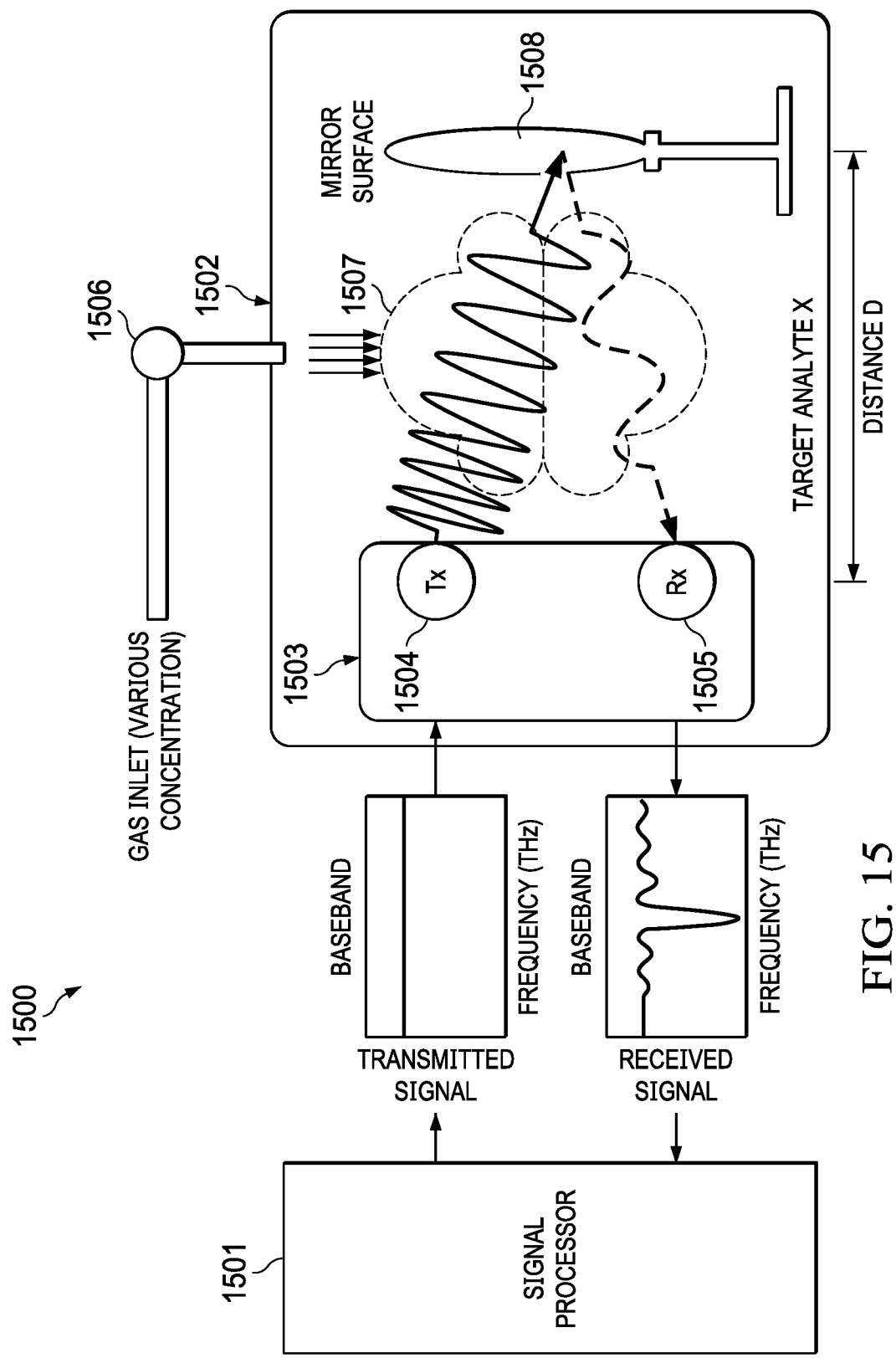
FIG. 15 is a block diagram illustrating the creation and use of a reference library of spectral responses for mapping measured absorption loss and path length to a gas concentration level, according to an embodiment.

FIG. 15 is a block diagram illustrating a calibration setup 1500 for the creation of a reference library for mapping measured absorption loss and path length to gas concentration level, according to an embodiment. The example calibration setup 1500 includes sealed, vacuum chamber 1502 with gas inlet 1506 for allowing various concentrations of a particular target gas 1507 into chamber 1502. Mirror surface 1508 located a known distance D from baseband receiver 1505 is used to reflect THz EM waves transmitted by baseband transmitter 1504 to baseband receiver 1505. The distance D can be adjusted to determine concentration levels as a function of absorption loss and path length. Using calibration setup 1500 for different gases, different gas concentration levels for different path lengths can be determined and organized into a reference library as shown in FIG. 16.

FIG. 16 is an example table 1600 of the reference library, according to an embodiment. Given the measure path length and measured absorption loss, the target gas concentration can be obtained from table 1600. For example, for each path length D various absorption losses (incremented by 5%) with corresponding target gas concentrations are included in table 1600. Path length can be measured using TOA calculations, where the TOA equals to the difference between the start time of receipt of the received signal by the baseband receiver and the start time of the transmitted signal multiplied by the speed of light. To determine concentration level, the measured absorption path loss and the measured absorption loss are used to index table 1600 to obtain the estimated concentration level for the gas. Interpolation can be used to estimate concentration levels for path lengths or measured absorption losses that are in between the data points in table 1600. In an embodiment, table 1600 is stored in memory on the electronic device, as described in reference to FIG. 17.

Figure 17:
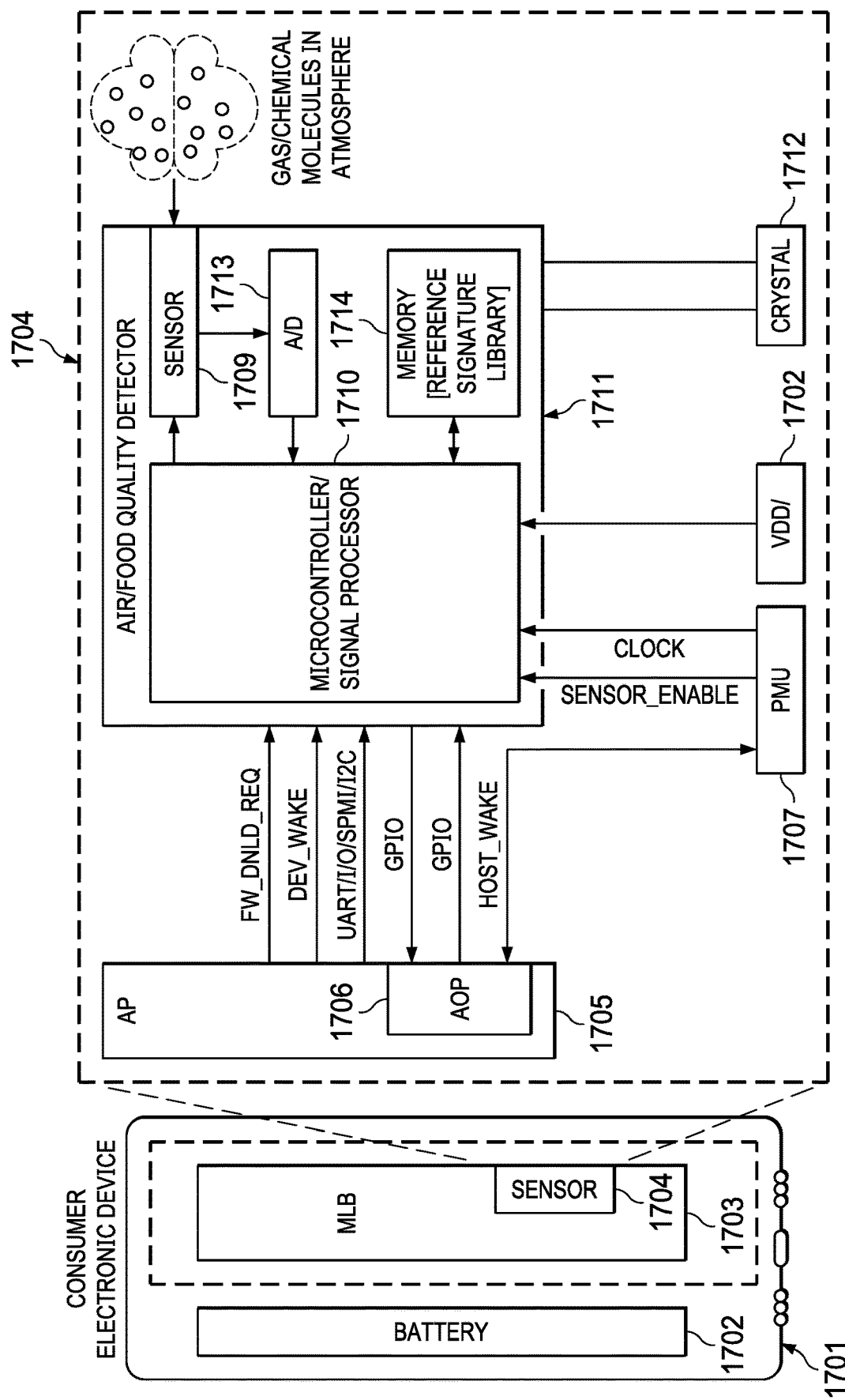
FIG. 17 is a schematic diagram of a mobile device system architecture for performing THz spectroscopy and imaging in a dynamic environment, according to an embodiment.

FIG. 17 is a schematic diagram of an architecture 1704 for performing THz spectroscopy and imaging in a dynamic environment, according to an embodiment. Architecture 1704 is shown implemented on printed circuit board 1703 installed in electronic device 1701, which in this example is a smartphone. Architecture 1704 includes application processor (AP) 1705, Always on Processor (AOP) 1706, air/food quality detector 1711 and power management unit (PMU) 1707. Air/food quality detector 1711 further includes microcontroller/signal processor 1710, memory 1714, THz sensor 1709 and analog-to-digital (A/D) converter 1713. Air/food quality detector 1711 is coupled to crystal oscillator 1712 and power source 1702 (e.g., battery 1702) and can be implemented as a SoC on electronic device 1701.

In an embodiment, AOP 1706 is coupled to microcontroller/signal processor 1710 using general purpose I/O (GPIO) pins. AOP 1706 is "always on" while consumer electronic device 1701 is operating. This allows for continuous sensing of, for example, gas concentrations in dynamic environments. In an application, a user carries electronic device 1701 on their person and if they enter an indoor environment that has an unhealthy concentration of a harmful gas (e.g., $CO_2$, CO), the user is automatically alerted through visual and/or audio feedback of the air/food quality on a display screen of mobile device 1701 and/or audible alarm played through audio subsystem of electronic device 1701 and/or force feedback through a haptic engine of electronic device 1701, as described in reference to FIG. 20.

In an embodiment, AOP 1706 is coupled to PMU 1707 and provides a HOST_WAKE signal to PMU 1707. In response to receiving the HOST_WAKE signal, PMU 1707 provides a SENSOR_EN signal to microcontroller/signal processor 1710 to enable air/food quality detector 1709. PMU 1707 also provides a clock signal to microcontroller/signal processor 1710.

In an embodiment, AP 1705 communicates with microcontroller/signal processor 1710 through a serial communication interface, such as UART, SPI or I2C. AP 1705 also provides a DEV_WAKE signal to wake-up microcontroller/signal processor 1710 and a FW_DNLD_REQ to microcontroller/signal processor 1710 to update firmware in memory 1714 for the sensor 1709. In an embodiment, memory 1714 stores target material spectral responses and the reference library described in reference to FIG. 1-16. Memory 1714 can be non-volatile memory such as flash memory.

In an embodiment, THz sensor 1709 is commanded by microcontroller/signal processor 1710 to emit EM waves in the THz frequency band into the dynamic environment, and receive THz EM waves reflected from one or more objects in the dynamic environment, as described in reference to FIGS. 1-16. The received signals are converted from analog to digital values by A/D converter 1713 and input to microcontroller/signal processor 1710.

Microcontroller/signal processor 1710 computes the spectral response of the received signal using a frequency transformation. An example frequency transformation is the Fast Fourier Transform (FFT) but other methods can also be used such as linear predictive coding (LPC).

Microcontroller/signal processor 1710 performs the compensation techniques described in reference to FIGS. 1-8 to remove impairments from the spectral response of the received signal due to environment and system loses. Microcontroller/signal processor 1710 then implements a matching algorithm on the absorption signature of the received signal and known target absorption signatures stored in memory 1714.

In an embodiment, the matching is done by comparing absorptions spectra in the frequency domain. For example, the reference library in memory 1714 records carbon monoxide (CO) as having an absorption spectra at frequency 0.692 THz. When the THz EM wave is transmitted, the system will determine from the absorption spectra of the reflected signal if the frequency of 0.692 THz has any absorption. A match occurs when absorption spectra is detected at 0.692 THz.

In an alternative embodiment, the matching of absorption signatures is accomplished by computing a Euclidean distance, or other suitable distance metric, between the measured absorption signature and each of the known absorption signatures stored in memory 1714. In an embodiment, the target transmission medium having an absorption signature that is the minimum Euclidean distance from the measured absorption signature is the best match. After a matching is found, Microcontroller/signal processor 1710 accesses a reference library of concentration levels stored in memory 1714 to estimate the concentration level of the matched transmission medium. Microcontroller/signal processor 1710 then reports the detected transmission medium and its estimated concentration level to AOP 1706. The reported information is used by an application running on AP 1705 to generate an alert on mobile device 1701 or perform any other desired task using the reported information. The alert can be in any desired format using any desired output device, including but not limited to: display screens, instant messaging, email, audio feedback and force feedback.

In an application, the electronic device can report the information to a centralized server that crowd sources similar information from many devices for a particular geographic area. For example, data can be harvested from multiple mobile devices operating at a disaster site (e.g., a building fire) through one or more wireless access points near the disaster site and the data can be combined and analyzed to determine the risk of exposure of first responders to dangerous gases/chemicals present at the disaster site.

In another application, architecture 1704 can be integrated into a smart speaker or other Internet of things (IoT) device. The device respond to user voice commands, such as "What is the carbon dioxide level in this room?" In an embodiment, the device can be integrated with a WiFi network so that multiple devices can be placed in different rooms/offices and report local gas concentration levels. In an embodiment, the device can detect smoke and/or dangerous gases/chemicals caused by a fire such as carbon monoxide (CO) or hydrogen cyanide (HC), and generate an alert and/or automatically call for emergency assistance.

Example Processes

FIG. 18 is a flow diagram of THz spectroscopy process 1800 in a dynamic environment, according to an embodiment. Process 1800 can be implemented by architectures 1700, 2000, as described in reference to FIGS. 17 and 20.

Process 1800 begins by emitting, by a transmitter of an electronic device, a continuous THz EM wave into a dynamic environment (1801), receiving, by a receiver of the consumer electronic device, a THz EM wave reflected from at least one object in the dynamic environment (1802), and computing, by one or more processors of the consumer electronic device, a spectral response of a received signal indicative of the reflective THz EM wave to determine an absorption spectra (1803), where the absorption spectra is indicative of a transmission medium in the dynamic environment that changes over time. Details of process 1800 is discussed in reference to FIGS. 1-16. An example hardware architecture for performing these steps was previously disclosed in reference to FIG. 17.

Process 1800 continues by identifying the transmission medium in the dynamic environment by matching the absorption spectra of the received signal with a known absorption spectra of a target transmission medium (1804). In an embodiment, to simplify comparisons between different gas species that differ in number of absorption peaks, a number of equal sized frequency bins of a histogram are constructed in the frequency range of 0.3 to 18.0 THz, with the frequency resolution based on the measurement data. This technique is described in H. Lin et al., "Gas recognition with terahertz time-domain spectroscopy and spectral catalog: a preliminary study," Terahertz Photonics (Nov. 29, 2007). An encoding technique is used where an absorption peak at a particular frequency marks the respective frequency bin with a Boolean one, otherwise the default value is a Boolean zero indicating no peak. Once the THz spectrum is encoded, the transmission medium in the dynamic environment is identified using a minimum Euclidean distance to target transmission mediums stored on the device. More particularly, the Euclidean distance between each respective frequency bin in the histogram is computed, combined and compared.

Process 1800 continues by determining, by the one or more processors, a concentration level of the identified target transmission medium (1805). For example, the gas concentration level can be determined by comparing the measured absorption loss and computed path length of the received signal with a reference library of gas concentration levels for the identified target transmission medium. A calibration setup can be used to empirically determine gas concentration levels for the reference library, as described in reference to FIGS. 15 and 16.

Figure 19B:
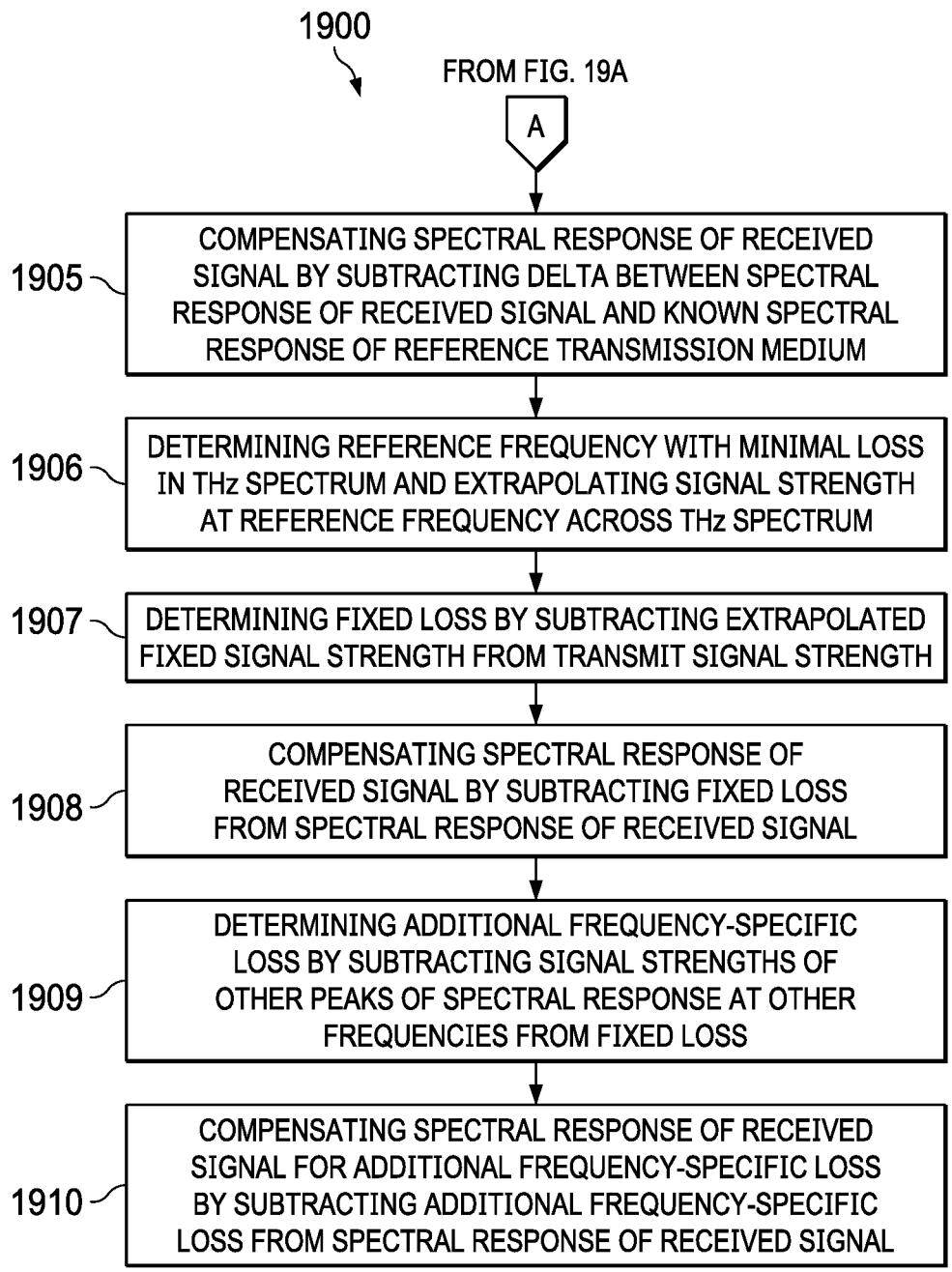

FIGS. 19A and 19B is a flow diagram of a first process 1900 of removing impairments from a spectral response of a received signal due to environmental and system losses. Process 1900 can be implemented by architectures 1700 and 2000, as described in reference to FIGS. 17 and 20, respectively.

Referring to FIG. 19A, process 1900 begins by obtaining the spectral response of a received signal (1901) and determining if a portion of the absorption spectra is below a noise floor of the baseband receiver (1902). In accordance with the absorption spectra being below the noise floor, using curve fitting to restore the portion of the absorption spectra below the noise floor (1903).

Referring to FIGS. 19A and 19B, in accordance with a portion of the absorption spectra not being below the noise floor or after restoring the portion below the noise floor using curve fitting, obtaining a known spectral response of a reference transmission medium (1904), and compensating the spectral response of the received signal by subtracting the delta between the spectral response of the received signal and the known spectral response of the reference transmission medium (1905).

Process 1900 continues by determining a reference frequency with minimal loss across the THz frequency spectrum and extrapolating the signal strength at that frequency across the THz frequency spectrum (1906), determining a fixed loss by subtracting the extrapolated fixed signal strength from the transmit signal strength (1907), and compensating the spectral response of the received signal by subtracting the fixed loss from the spectral response of the received signal (1908).

Process 1900 continues by determining additional frequency-specific loss by subtracting signal strengths of other peaks of the spectral response of the received signal at other frequencies from the fixed loss (1909), and compensating the spectral response of the received signal for the additional frequency-specific loss by subtracting the additional frequency-specific loss from the spectral response of the received signal (1910).

Embodiments for Optimizing System Performance

In an embodiment, it is desirable to optimize the performance of the THz system described in reference to FIGS. 1-19. If the THz system is included in a modern consumer electronic device (e.g., smartphone) there is typically multiple onboard sensors that can be used to assist in optimizing THz system performance. For example, motion sensors (e.g., accelerometers, gyros) can be used to adjust the duty cycle of THz wave scanning to improve battery performance, and ambient sensors (e.g., pressure sensor, temperature sensor, humidity sensor) to reduce the impact of environmental factors (e.g., change in humidity or atmospheric pressure) on detection accuracy. Localization techniques (e.g., cellular, satellite-based, WiFi) are used to account for county or country regulations/standards. An example of localization technology is a global positioning system (GPS) receiver chip that provides geopositioning.

Figure 20A:
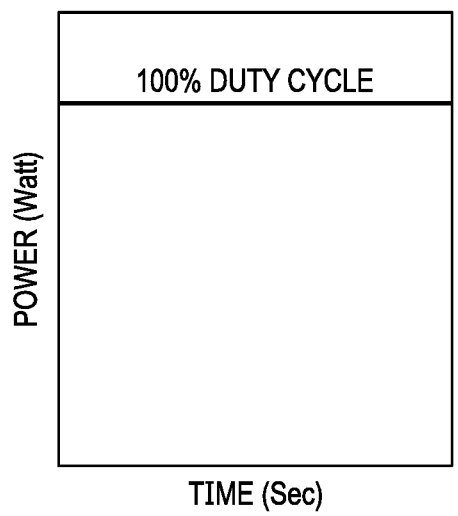
FIGS. 20A and 20B are plots illustrating battery consumption versus duty cycle for an electronic device that performs THz scans, according to an embodiment.
Figure 20B:
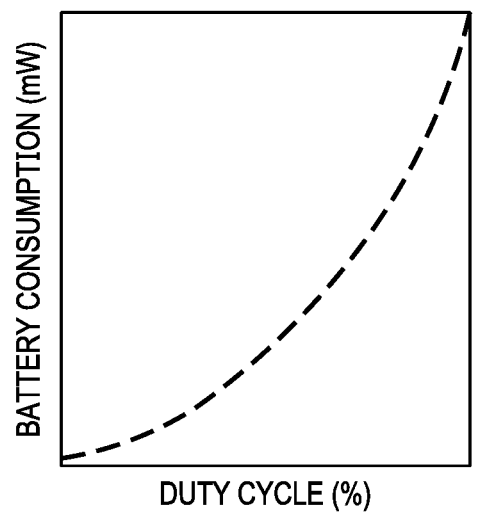

FIGS. 20A and 20B are example plots illustrating battery consumption versus duty cycle for an electronic device that performs THz scans, according to an embodiment. FIG. 2A illustrates power consumption over time with THz scanning at a 100% duty cycle (i.e., always scanning), and FIG. 21B illustrates the increase in battery consumption with an increase in duty cycle percentage. As illustrated in FIGS. 20A and 20B, improvement to battery performance can be accomplished by reducing the duty cycle for THz scanning, as described in reference to FIGS. 21-28.

Figure 20C:
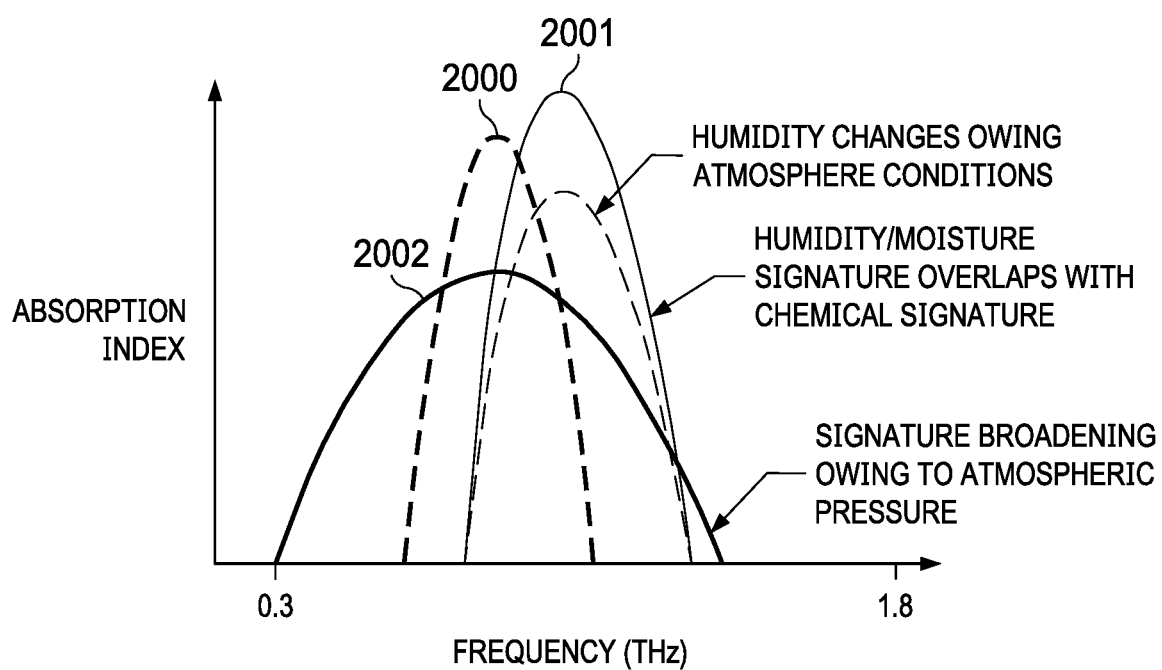
FIG. 20C is a plot illustrating the impact of environmental factors on a chemical signature, according to an embodiment.

FIG. 20C is an example plot illustrating the impact of environmental factors on a gas signature, according to an embodiment. Humidity/moisture signature 2001 overlaps with gas signature 2000 and can change due to atmospheric conditions (see dashed line). Additionally, atmospheric pressure can cause the frequency band of gas signature 2000 to widen 2000. Accordingly, atmosphere conditions can impact the detection accuracy of the THz system. In an embodiment, additional processing of the reflected THz EM waves is performed to reduce the impact of atmospheric conditions on the detection accuracy of the THz system, as described below, as described in reference to FIGS. 29 and 30.

Figure 21A:
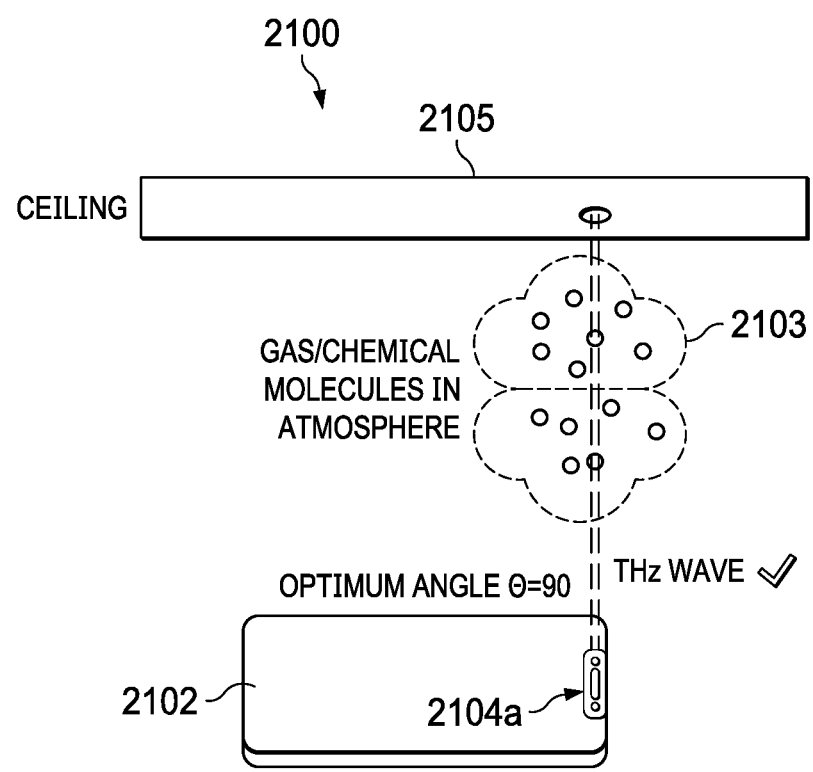
FIGS. 21A and 21B illustrate the use of motions sensors of an electronic device to improve battery performance when the device is stationary and face up and when the device is stationary and face down, according to an embodiment.
Figure 21B:
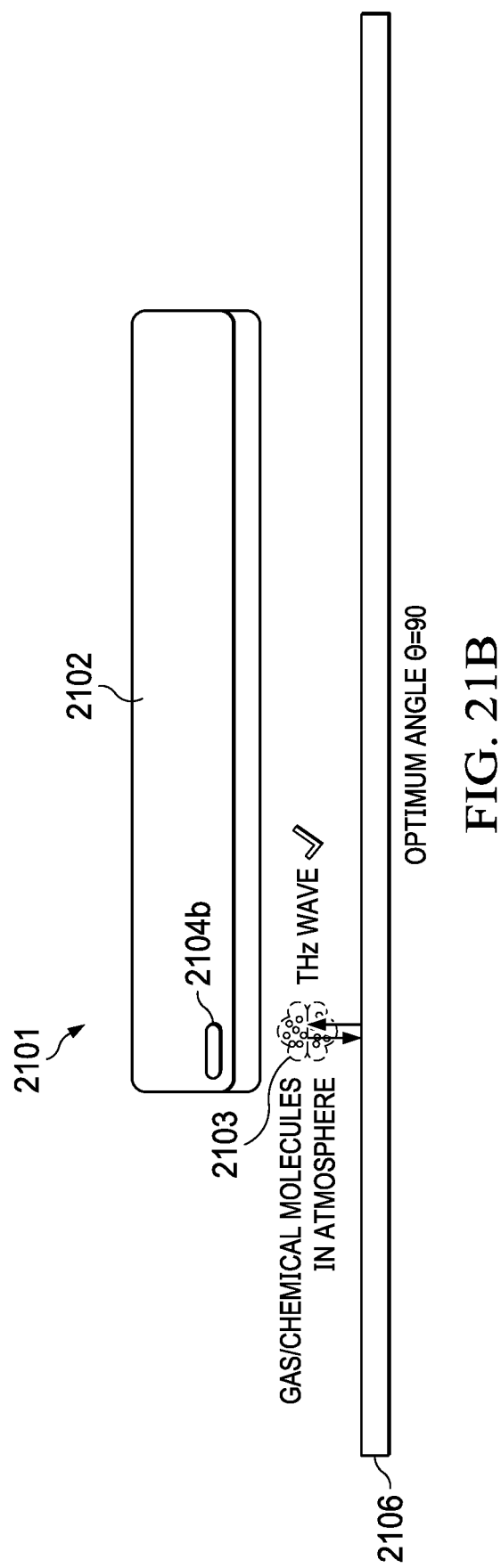

FIGS. 21A and 21B illustrate the use of motions sensors of an electronic device to improve battery performance when the device is stationary and face up and when the device is stationary and face down, according to an embodiment. Referring to FIG. 21A, consumer electronic device 2102 is stationary (e.g., placed on a surface) and facing up towards ceiling 2105. In this orientation ($\theta$=90°), a first THz transceiver 2104a of electronic device 2102 emits a THz EM wave that reflects off ceiling 2105. The reflected THz EM wave travels through transmission medium 2103 (e.g., chemical molecules in atmosphere) and is received by THz transceiver 2104a. Because there is a zero angle of incidence with ceiling 2105 the reflected THz EM wave suffers less signal loss due to the impact with ceiling 2105. Also, assuming there are no reflective objects between THz transceiver 2104a and ceiling 2105, there is no signal loss due to additional path delays caused by additional reflections off other reflective objects.

Referring to FIG. 21B, electronic device 2102 is stationary and facing down toward floor 2106. In this orientation ($\theta$=90°), a second THz transceiver 2104b of consumer electronic device 2102 emits a THz wave that reflects off floor 2106. The reflected THz wave travels through transmission medium 2103 and is received by THz transceiver 2104b. Because there is a zero angle of incidence with floor 2106 the reflected THz wave suffers less signal loss due to the impact with floor 2106. Also, assuming there are no reflective objects between THz transceiver 2104b and floor 2106, there is no signal loss due to additional path delays caused by additional reflections off other objects.

In an embodiment, one or more motion sensors (e.g., accelerometer, gyro, laser, infrared sensor, optical sensor) can detect when consumer electronic device 2102 is stationary and pointing towards ceiling 2105 or floor 2106 as illustrated in FIGS. 21A, 21B, and then reduce the duty cycle of the THz scan. For example, during a THz scan cycle THz transceiver 2104 sweeps out an angular arc between two limits (e.g., 0° to 180°). A multi-axis accelerometer of the electronic device 2102 can determine a gravity vector and/or a multi-axis gyroscope can determine the orientation of the electronic device 2102 in local-level reference coordinate frame. If electronic device 2102 remains stationary for a specified period of time (e.g., 30 seconds), the duty cycle of the THz scan is reduced to conserve battery power, as described more fully in reference to FIGS. 22A and 22B.

Figures 22A, 22B:
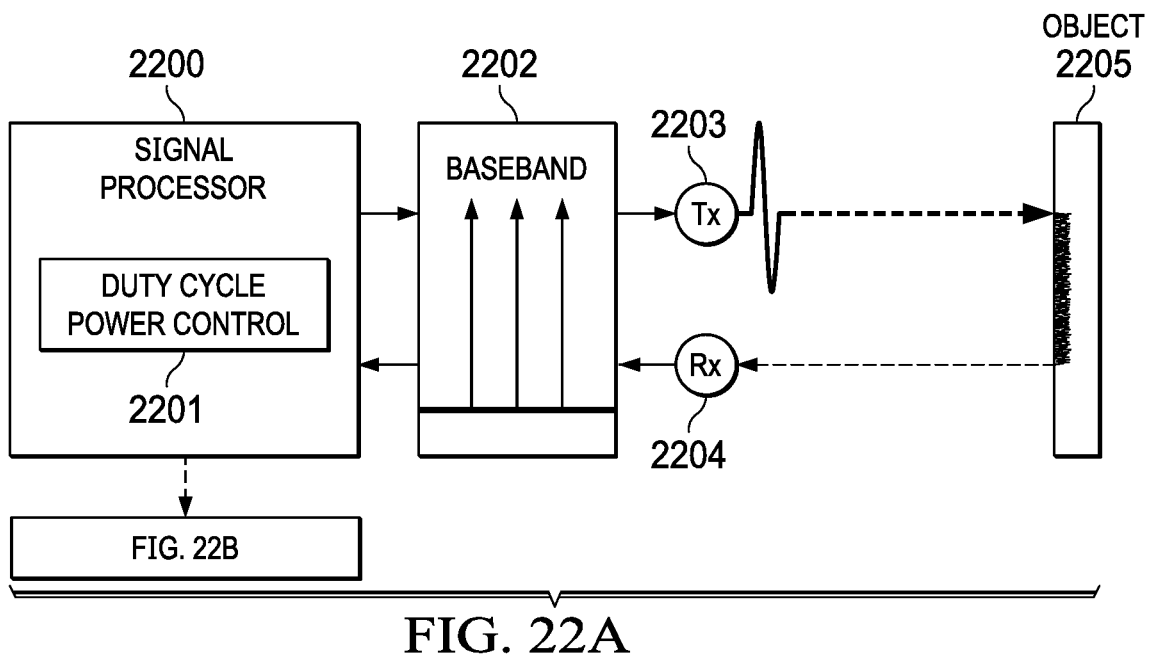
FIGS. 22A and 22B illustrate adjusting THz scan duty cycle to save power, according to an embodiment.

FIGS. 22A and 22B illustrate adjusting a THz scan duty cycle to save power, according to an embodiment. FIG. 22A shows a THz system that includes signal processor 2200 THz transmitter 2203, THz receiver 2204 and duty cycle power control unit 2201. THz baseband signals 2202 are transmitted by THz transmitter 2203 and are reflected off object 2205. The reflected THz signals are received by THz receiver 2204 and processed by signal processor 2200, as previously described in FIG. 1A. Duty cycle power control unit 2201 adjusts the duty cycle of the THz scan if the electronic device is not connected to a non-battery power source (e.g., a wall outlet). In an embodiment, power control unit 2201 tests for the following example conditions:

If the electronic device is static fort <X second; scan at 100% duty cycle,
If the electronic device is static fort >X seconds: scan at 50% duty cycle,
If the electronic device is static fort >X+Y seconds: scan at 25% duty cycle.

Figure 30:
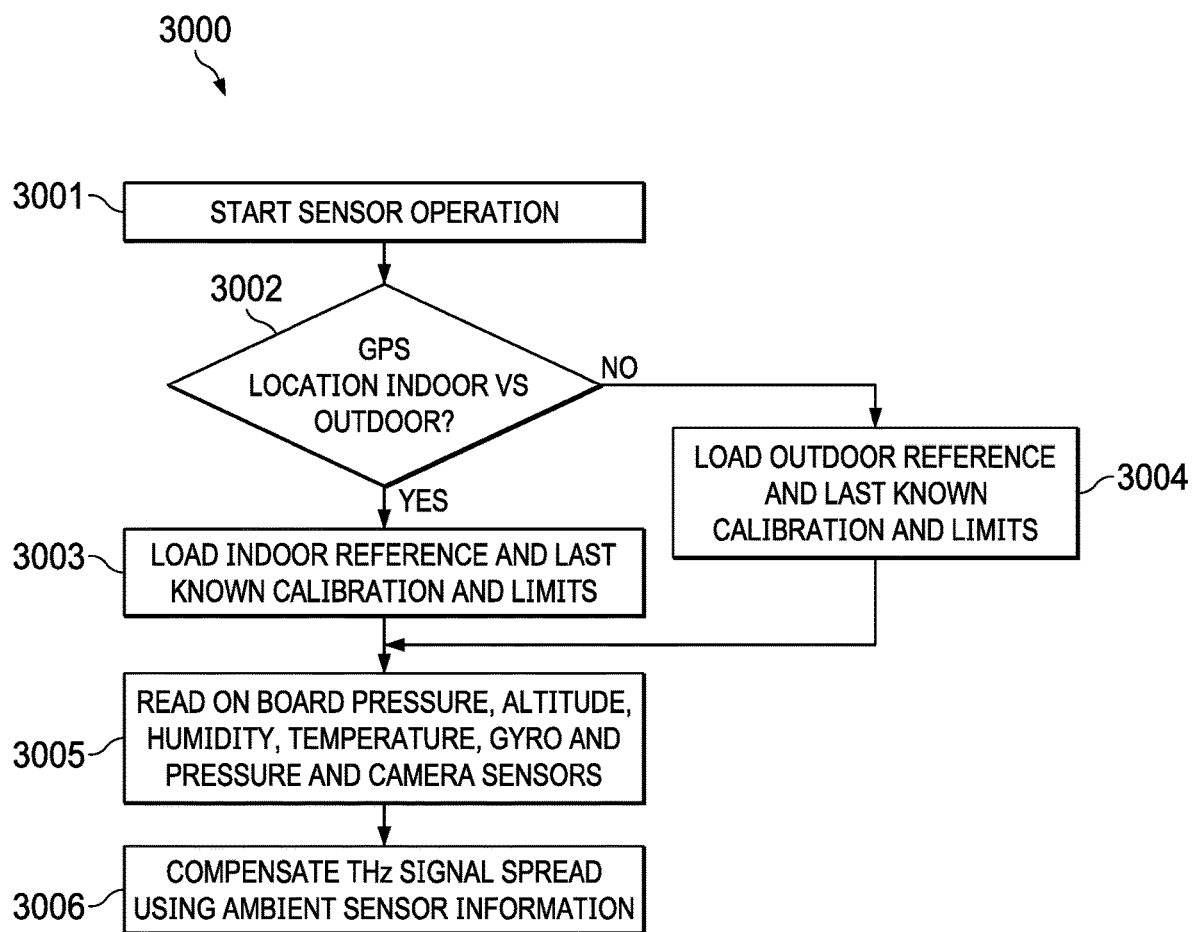
FIG. 30 is a flow diagram illustrating using location-based information to optimize THz spectroscopy and imaging, according to an embodiment.

If the electronic device is connected to a non-battery power source, the THz scan is operated at 100% duty cycle or a selective tone transmission, such as described in reference to FIG. 30. The duty cycles referenced above are only exemplary and any desired percentage reduction of duty cycle can be used and any desired values for the variables X and Y can be used.

Figure 23A:
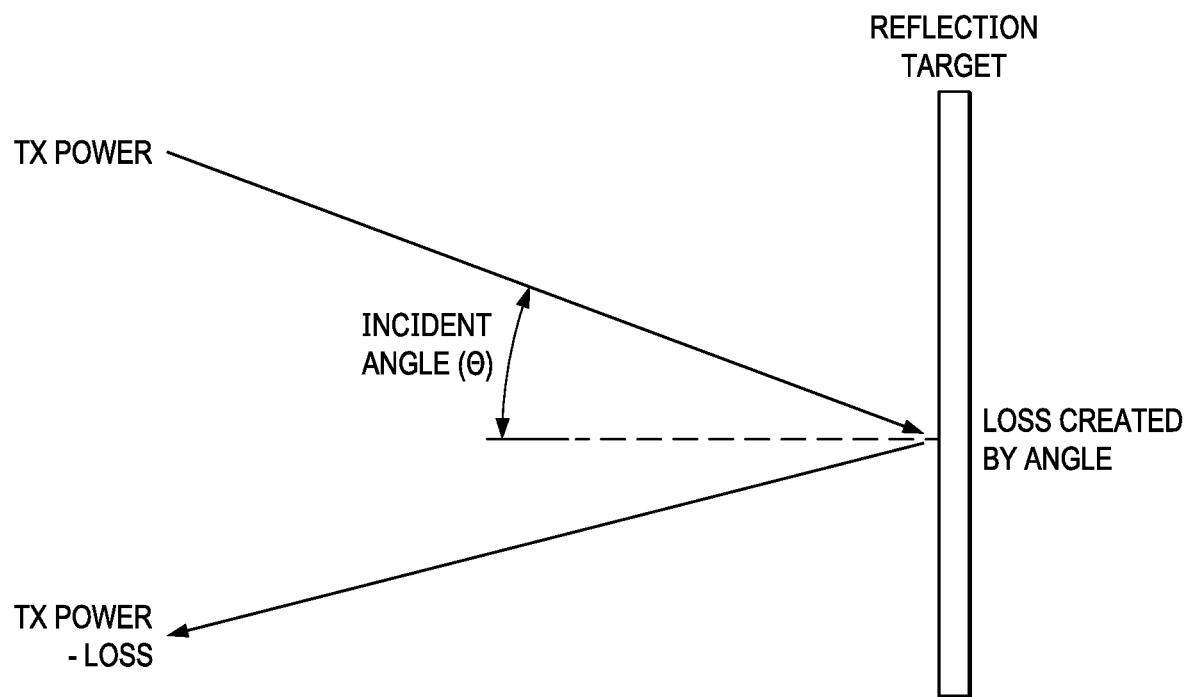
FIGS. 23A and 23B illustrates transmission power loss as a function of incident angle, according to an embodiment.
Figure 23B:
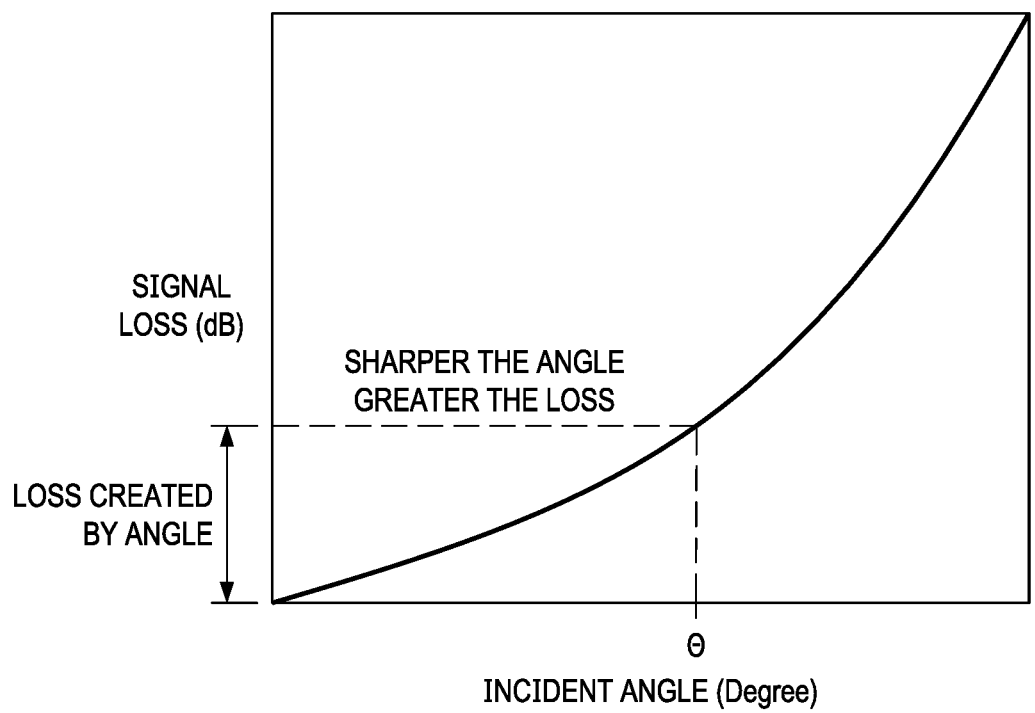

FIGS. 23A and 23B illustrate transmission power loss as a function of incident angle using adaptive beam scanning to save power, according to an embodiment. As illustrated in FIG. 23A, path loss increases as the incident angle at the reflection point at the object increases, resulting in power loss in the reflected signal. The sharper the incident angle the greater the loss, as shown in FIG. 23B.

Figure 24A:
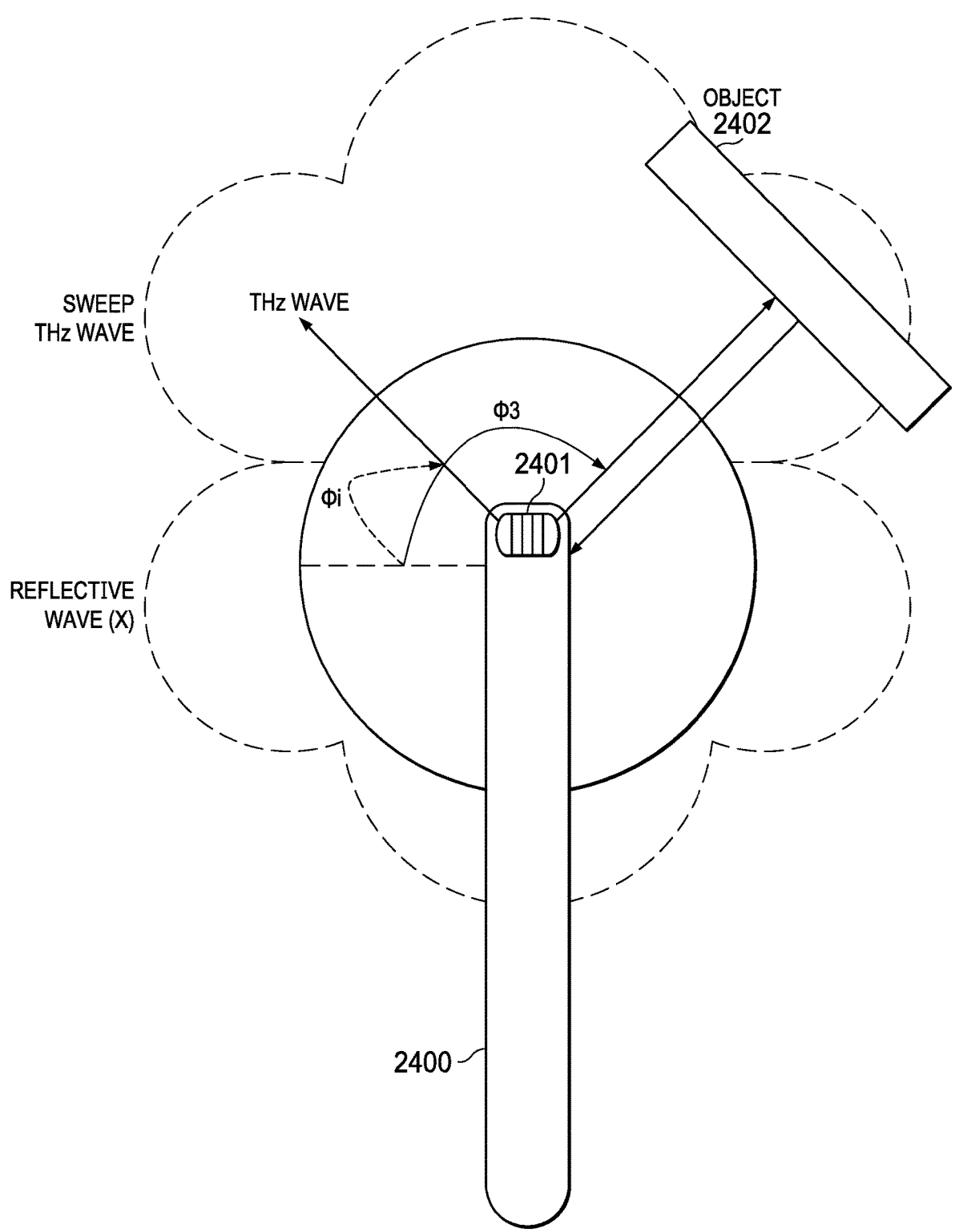
FIGS. 24A and 24B illustrate sweeping a THz EM wave to build a reflective signal strength table, according to an embodiment.
Figure 24B:
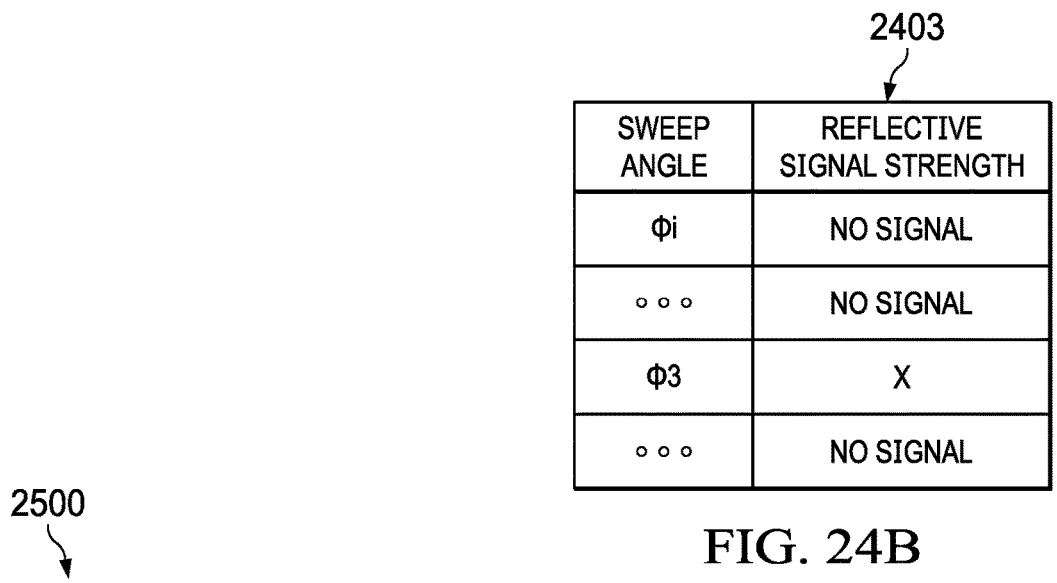

FIGS. 24A and 24B illustrate sweeping a THz wave to build a reflective signal strength table, according to an embodiment. For the THz system to accurately detect a gas concentration, THz transceiver 2401 of electronic device 2400 emits a THz wave that is swept through a range of scan angles to build a table of reflective signal strengths. For each sweep angle $\phi_i$ the strength of the reflective signal (e.g., in dB) received by THz transceiver 2401 and its corresponding sweep angle are recorded in data structure 2403 (e.g., a table) stored in memory of the electronic device. In the example shown, there is a reflective signal at $\phi3$ due to object 2402. No other reflected signals were detected during this example THz scan. Any desired resolution for recording the sweep angle can be used, such as recording every x degrees of sweep (e.g., 5 degrees).

After data structure 2403 is built, the contents of data structure 2403 are used to direct THz transceiver 2401 to emit a THz wave only at the scan angle(s) recorded in the data structure 2403. Accordingly, the electronic device scans the environment in which it is located to determine scan angles where reflected THz signals are detected. By only scanning at recorded scan angles, battery power is conserved.

Figure 25:
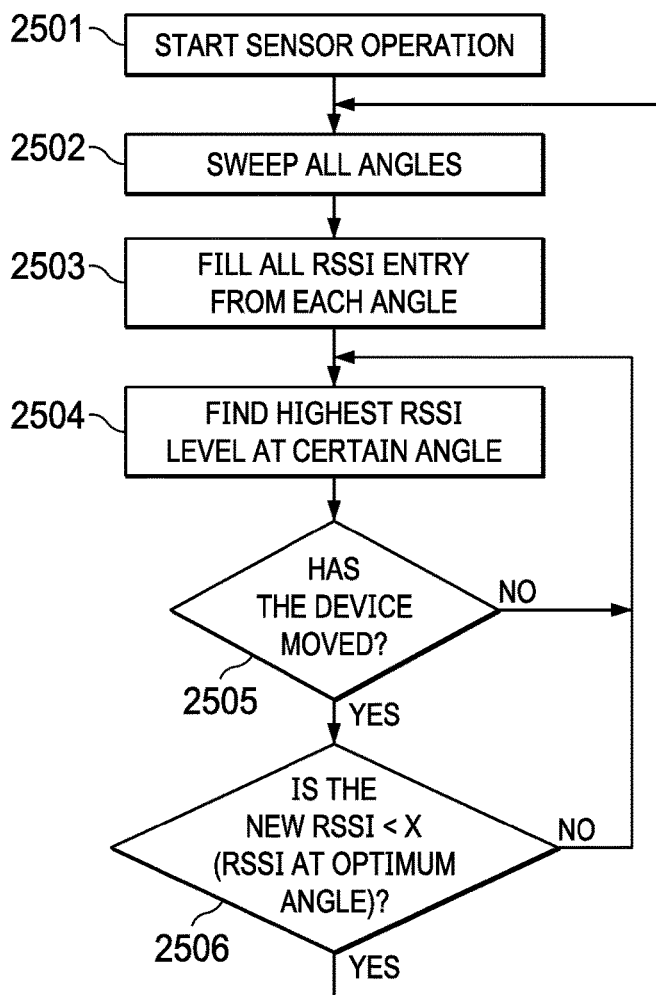
FIG. 25 is a flow diagram illustrating an adaptive beam scan to determine an optimum sweep angle to improve battery performance, according to an embodiment.

FIG. 25 is a flow diagram illustrating an adaptive beam scan process 2500 to determine an optimum sweep angle to improve battery performance, according to an embodiment.

Process 2500 begins by starting THz sensor operation (2501) and transmitting a sweeping THz wave through a plurality of scan angles (2502) referred to hereinafter as a "full scan." In an embodiment, the sensor operation is started automatically or manually by a user through an application running on the electronic device. The sensor operation can be started automatically based on a schedule and/or trigger event. The extent of the sweep is determined by the number and placement of THz transmitters on the electronic device. For example, if two transmitters are facing opposite directions on the electronic device, then potentially a 360° sweep around the electronic device can be performed.

Process 2500 continues by detecting received signal strengths at each scan angle and recording 2503 the signal strength and angle in a data structure. In an embodiment, the data structure is a look-up table (LUT) where each row is a scan angle.

Process 2500 continues by finding the highest received signal strength entry in the data structure at a specified scan angle (2504). Hereinafter, the specified angle is referred to as the "optimum angle." For example, the table can be sorted based on received signal strength, such that the optimum angle is at the top of the LUT. The electronic device then transmits a THz EM wave for spectroscopy only at the optimum angle to conserve battery power.

Process 2500 continues by determining if the electronic device has moved (2505). For example, one or more motion sensors (e.g., an accelerometer) can be used to determine of the electronic device has moved. If the electronic device has not moved, process 2500 returns to step 2504 and the same optimum angle found in step 2504 is used to transmit the THz EM wave for spectroscopy.

If the electronic device has moved, process 2500 checks if the highest received signal strength is less than the received signal strength found at the previous optimum angle X (2506). If the highest received signal strength is less than a received signal strength at the previous optimum angle X, process 2500 returns to step 2502 to perform another full scan and determine a new optimum angle based on the results of the full scan.

Accordingly, a full scan of received signal strengths for all angles is performed a first time to fill the data structure during an initialization phase. After the initialization phase, a full scan is only performed when the electronic device is detected by an onboard motion sensor as moving, and the highest received signal strength is less than the received signal strength at the previous optimum angle.

Figure 26A:
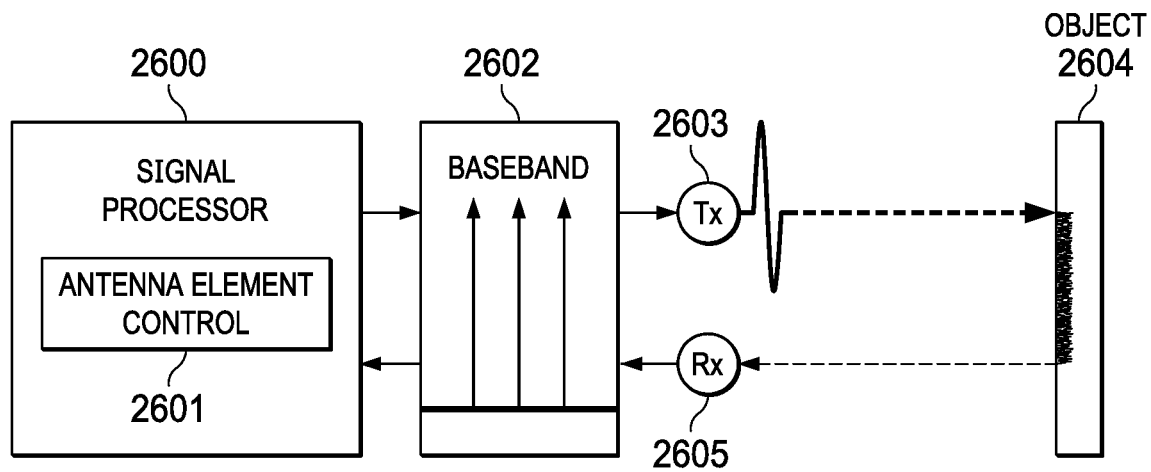
FIGS. 26A and 26B illustrate adaptive transmit power output control to improve battery performance, according to an embodiment.
Figure 26B:
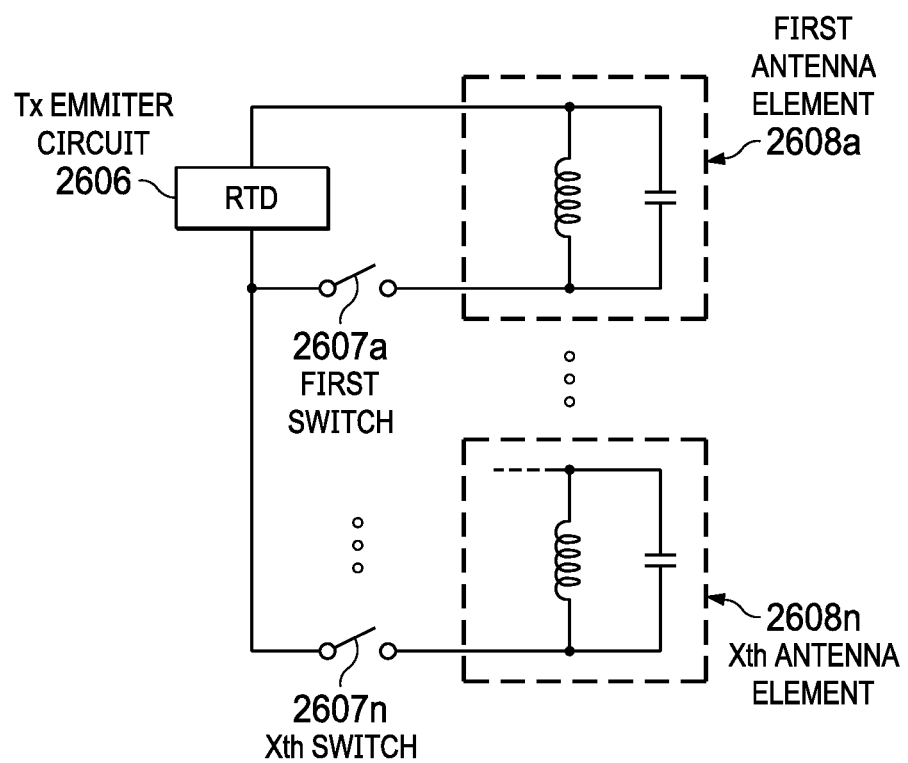

FIGS. 26A and 26B illustrate adaptive transmit power output control to improve battery performance, according to an embodiment. In an embodiment, a THz system includes signal processor 2600, THz transmitter 2603, THz receiver 2605 and antenna element control module 2601. Signal processor 2600 generates a baseband signal 2602 that is transmitted by THz transmitter 2603 into the environment, where it is reflected by object 2604. The reflected THz wave is received by THz receiver 2605 and processed by signal processor 2600, as previously described. In an embodiment, antenna control element is configured to reduce the number of antenna elements in THz transmitter 2603 to reduce battery consumption. For example, if the electronic device is static for t<X seconds, all the antenna elements are used and the transmission of the THz wave is at full power. If the electronic device is static for t>X seconds, and the SNR is greater than a threshold value, the transmit power is reduced by reducing the number of antenna elements used to transmit the THz EM wave.

Referring to FIG. 26B, an example embodiment of an antenna circuit for adaptive transmit output power is shown. The antenna circuit includes receiver/transmitter device (RTD) 2606, switches 2607a . . . 2607n and antenna elements 2608a . . . 2608n. Antenna element control 2601 sends control signals to switches 2607a . . . 2607n to open or close to add or remove antenna elements 2608a . . . 2608n from the path of RTD 2606, respectively. The more antenna elements used in the transmission of the THz EM wave, the more transmit signal power available and the more battery power consumed, as illustrated by the plot in FIG. 27. Conversely, removing antenna elements 2608a . . . 2608n from the path of RTD 2606, reduces battery power consumption but at the expense of less transmit signal power.

In embodiment, the THz system can operate in a "sniff mode" where THz EM waves are transmitted at discrete known frequencies of defined target gases that have a unique and maximum absorption spectra to improve battery performance, according to an embodiment. As previously stated, THz transceivers typically sweep across the whole THz band of frequencies to detect the presence of a target gas. However, sweeping the entire THz frequency band (0.3 THz to 18 THz) for every scan penalizes battery performance. To improve battery performance, a "sniff" mode is used by the THz system to transmit known discrete frequencies to which defined target gases have unique and maximum absorption spectra. In an embodiment, the THz system uses bias-controlled varactor 3007 for frequency tuning, as described in reference to FIG. 28B. In an embodiment, the discrete frequencies of known target gases are assessed from a table or other data structure stored on the electronic device.

Figure 28A:
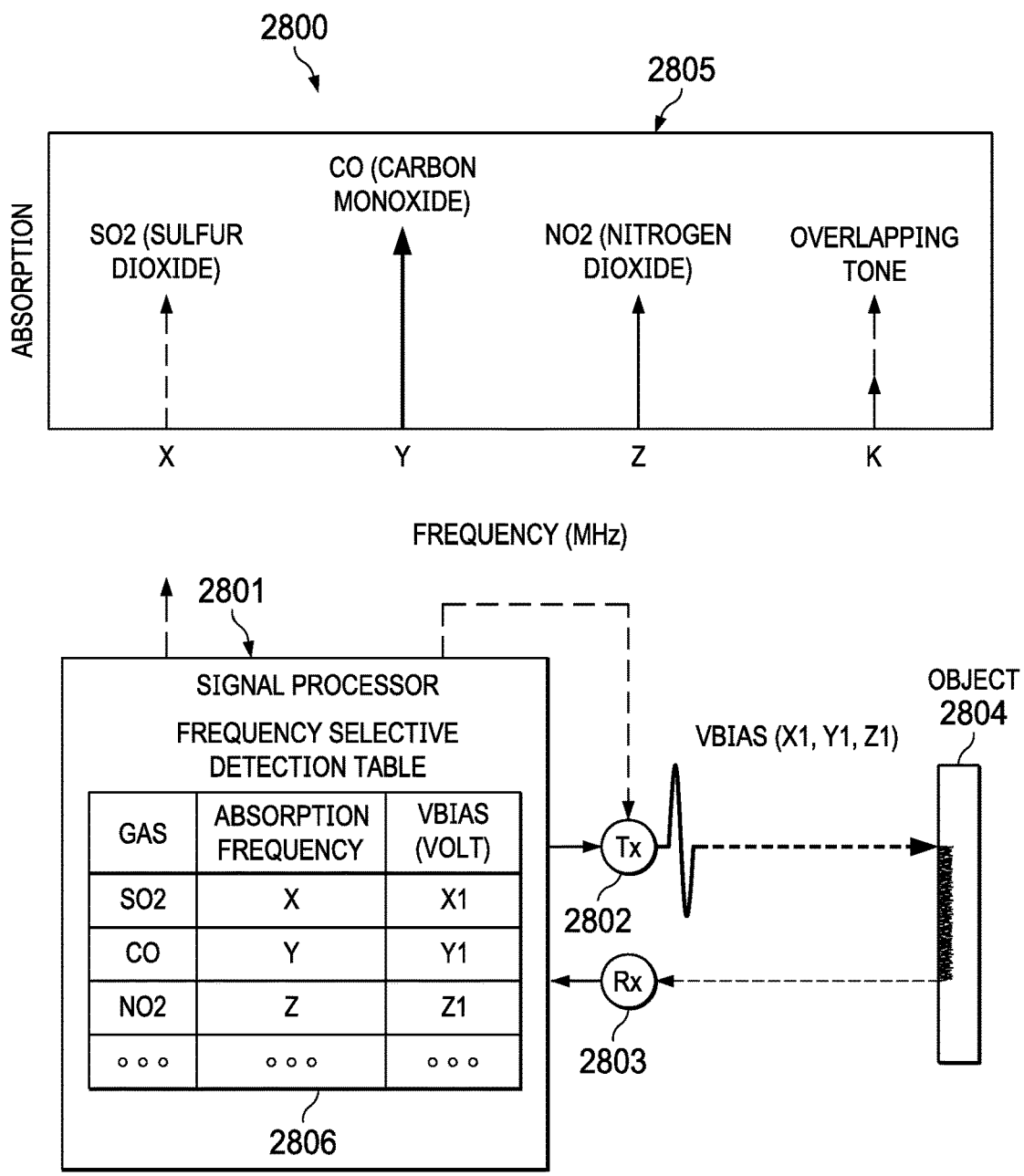
FIG. 28A illustrates a "sniff mode" where THz EM waves are transmitted at discrete known frequencies of defined target chemicals that have unique and maximum absorption spectra to improve battery performance, according to an embodiment.

Referring to FIG. 28A, signal processor 2801 stores a frequency selected detective look-up table 2806 that includes a voltage bias ($V_{bias}$) for each target gas. For example, each row of the table 2806 is associated with a target gas and includes a column for absorption frequency and a column for $V_{bias}$ (volts). Table 2806 can be updated using OTA technology by an online service. In an embodiment, table 2806 is updated based on the location of the electronic device. In an embodiment, table 2806 can be updated with known target gas data by a local area network or beacon when the electronic device is operating at the location or first enters the location. In the example shown, SO2 gas is associated with $V_{bias}$ X1, CO gas is associated with $V_{bias}$ X2 and NO2 gas is associated with $V_{bias}$ X3, as shown in table 2806. Signal processor 2801 retrieves the $V_{bias}$ values and sends them to THz transmitter 2802, which includes bias-controlled varactor circuit 3007 shown in FIG. 28B. The $V_{bias}$ values cause circuit 2807 to resonate at discrete frequencies X, Y and Z, for SO2, CO, NO2, respectively, as shown in the frequency plot 2805. Also shown are overlapping tones K, which the system intends to avoid. The result is that THz system transmits THz EM waves at discrete known frequencies for target gases, the reflections of those THz EM waves are received by THz receiver 2803 and signal processor 2801 computes the spectral responses of reflected signals as previously described.

Accordingly, the "sniff" mode, allows the THz system to: 1) prevent overlapping tones of different gases to improve detection accuracy; 2) save battery power, as the transmitter transmits only at the selected frequencies in table 2806; 3)

reduce sweep time as it does not require to scan a large frequency band, which is critical in dynamic environments as the THz sensor is not stationary for extended period of time; and 4) use bias controlled varactor to allow coarse and fine frequency tuning which allows for improved gas signature detection.

Figure 28B:
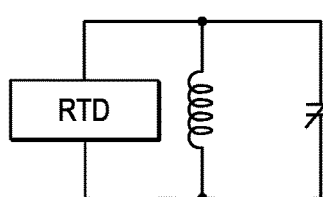
FIG. 28B is schematic diagram of a bias-controlled varactor circuit for transmitting discrete THz EM waves, according to an embodiment.

FIG. 28B is schematic diagram of a bias-controlled varactor circuit 2807 for transmitting discrete THz EM waves, according to an embodiment. RTD 2808 is coupled to coil 2809 and variable capacitor 2810. The absorption frequencies X, Y and Z shown in FIG. 28A can be obtained by adjusting the variable capacitor 2810 to different values, resulting in a different resonant frequency for each gas. Variable capacitor 2810 can be changed by, for example, microcontroller/signal processor 1710 described in reference to FIG. 17.

Figure 29A:
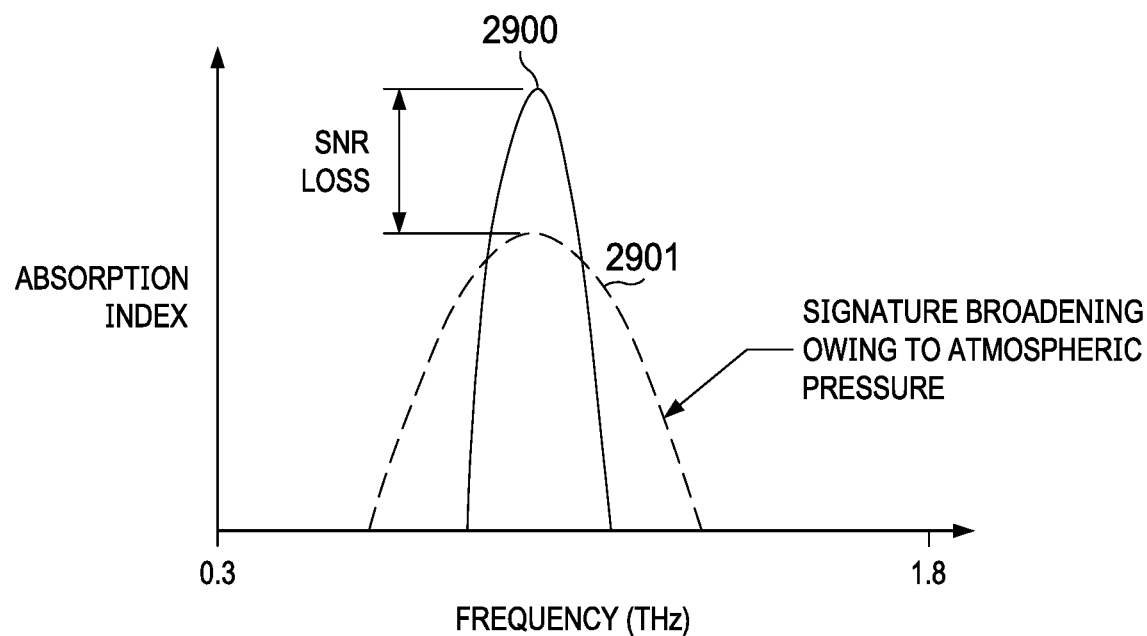
FIGS. 29A and 29B illustrate using ambient sensors to enable compensation of spectral responses impaired by environmental factors, according to an embodiment.
Figure 29B:
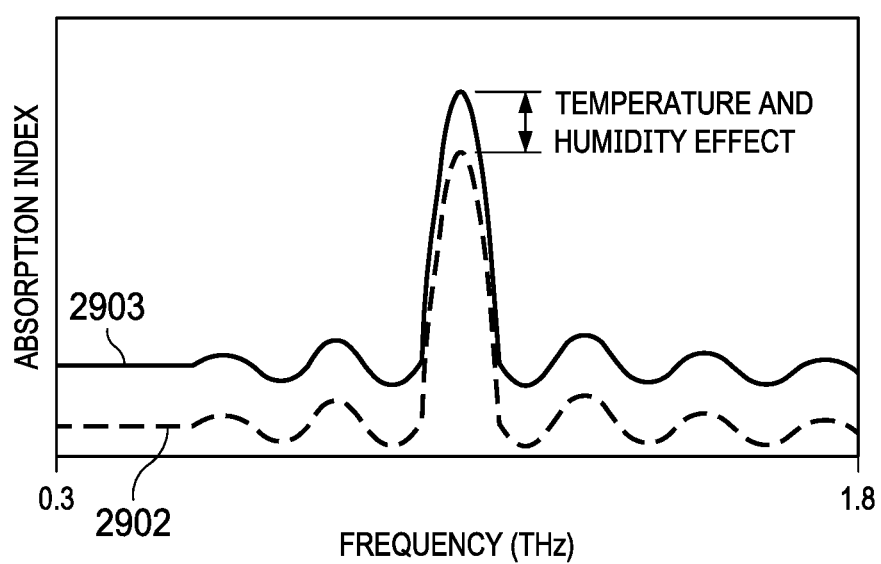

FIGS. 29A and 29B illustrate using ambient sensors to enable correction for impact from environmental factors, according to an embodiment. In an embodiment, onboard sensors (e.g., pressure, temperature and humidity sensors) are used to enable correction for impact from environmental factors. For example, a pressure sensor reading can be used to correct for the signal spread for target gas signatures, a humidity sensor can be used to remove spectral contributions from humidity/moisture in the spectral response of the reflected THz signal and temperature sensor reading can be used to compensate for SNR loss due to thermal losses.

Referring to FIG. 29A, the broadening of the frequency band of a gas signal due to atmospheric pressure is illustrated. An increase in atmospheric pressure results in a SNR degradation and widening of spectral degradation. Similarly, the effect of temperature and humidity on the spectral response of the received signal is illustrated. The spectral response is shifted vertically resulting in an SNR loss, as shown in FIG. 29B.

In an embodiment, a table of SNR loss for various readings of pressure, humidity and temperature. During operation, pressure, temperature and humidity readings from onboard sensor readings are used to index the table to obtain corrections that are applied to the spectral response of the received THz signal reflected from the environment, and thus reduce the impact of environmental factors on detection accuracy.

FIG. 30 is a flow diagram illustrating a process 3000 of using location-based information to optimize THz sensing, according to an embodiment.

Process 3000 begins by starting THz sensor operation (3001) and determining whether the electronic device is indoors or outdoors (3002). For example, one or more of satellite signal strength data, map data, radio frequency beacons and the presence or absence of WiFi signals is used to automatically determine if the electronic device is operating indoors or outdoors. In an embodiment, manual user input (touch or speech input) is used to inform the THz system that the electronic device is indoors.

In accordance with the electronic device operating indoors, loading indoor gas reference data and last known calibration and gas concentration limits associated with county or country specific regulations or standards (3003). In accordance with the electronic device operating outdoors, outdoor gas reference data and last known calibration and gas concentration limits are obtained by the THz system (3004). The reference gas data can be for a known gas (e.g., O2, N) at the location, as described in reference to FIGS. 5A-5C. The last known calibration data can be recorded by the electronic device at the location and stored in a table or other data structure on the electronic device. In an embodiment, the gas concentration limits are preloaded during manufacture and updated over-the-air (OTA) by an online update service for the electronic device.

Process 3000 continues by obtaining onboard ambient/motion sensor readings (3005) and compensating the spectral response of the received THz signal using the ambient/motion sensor readings (3005). For example, the amplitude or frequency band of the spectral response can be adjusted to compensate for the changes to the spectral response in amplitude and frequency band due to environmental factors.

Exemplary Device Architecture

Figure 31:
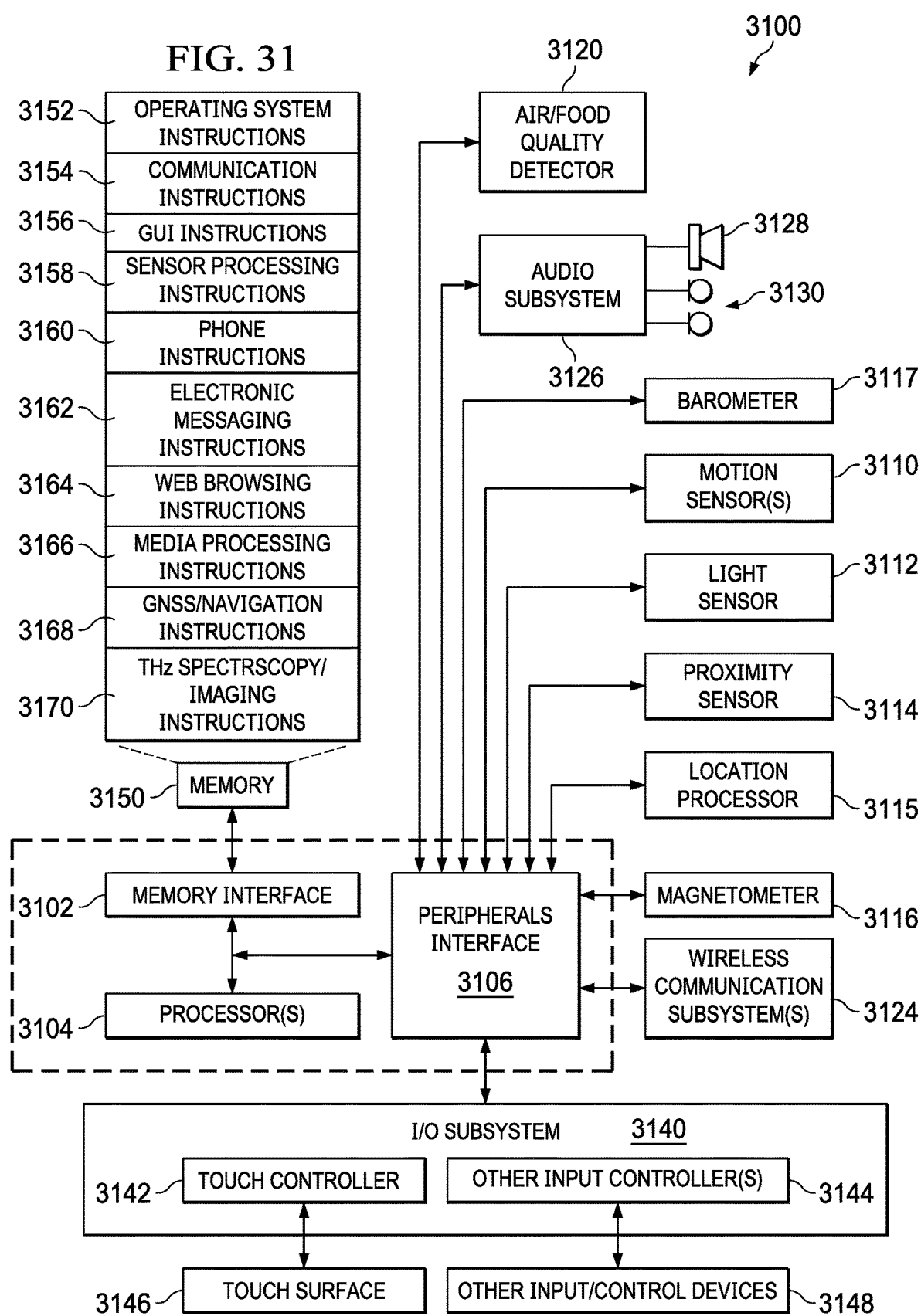
FIG. 31 illustrates an example electronic device architecture implementing the features and operations described in reference to FIGS. 1-30, according to an embodiment.

FIG. 31 illustrates example electronic device architecture 3100 implementing the features and operations described in reference to FIGS. 1-30. Architecture 3100 can include memory interface 3102, one or more data processors, image processors and/or processors 3104 and peripherals interface 3106. Memory interface 3102, one or more processors 3104 and/or peripherals interface 3106 can be separate components or can be integrated in one or more integrated circuits.

Sensors, devices and subsystems can be coupled to peripherals interface 3106 to provide multiple functionalities. For example, one or more motion sensors 3110, light sensor 3112 and proximity sensor 3114 can be coupled to peripherals interface 3106 to facilitate motion sensing (e.g., acceleration, rotation rates), lighting and proximity functions of the wearable computer. Location processor 3115 can be connected to peripherals interface 3106 to provide geo-positioning. In some implementations, location processor 3115 can be a GNSS receiver, such as the Global Positioning System (GPS) receiver. Electronic magnetometer 3116 (e.g., an integrated circuit chip) can also be connected to peripherals interface 3106 to provide data that can be used to determine the direction of magnetic North. Electronic magnetometer 3116 can provide data to an electronic compass application. Motion sensor(s) 3110 can include one or more accelerometers and/or gyros configured to determine change of speed and direction of movement of the wearable computer. Barometer 3117 can be configured to measure atmospheric pressure around the mobile device. Air/food quality detector 3120 (see FIG. 17) can be configured to perform the THz spectroscopy and imaging described in reference to FIGS. 1-30.

In an embodiment, a digital image capture device and a depth sensor (both not shown) can be coupled to peripherals interface 3106. The digital image capture device (e.g., a video camera) captures images (e.g., digital photos, video clips) and depth sensor (e.g., infrared, LIDAR) capture depth data (e.g., point cloud data) for rendering three-dimensional scenes for augmented reality (AR) and virtual reality (VR) applications.

Communication functions can be facilitated through wireless communication subsystems 3124, which can include radio frequency (RF) receivers and transmitters (or transceivers) and/or optical (e.g., infrared) receivers and transmitters. The specific design and implementation of the communication subsystem 3124 can depend on the communication network(s) over which a mobile device is intended to operate. For example, architecture 3100 can include communication subsystems 3124 designed to operate over a GSM network, 3G, 4G, 5G, a GPRS network, an EDGE network, a WiFi™ network, near field (NF) and a Bluetooth™ network. In particular, the wireless communication subsystems 3124 can include hosting protocols, such that the mobile device can be configured as a base station for other wireless devices.

Audio subsystem 3126 can be coupled to a speaker 3128 and a microphone 3130 to facilitate voice-enabled functions, such as voice recognition, voice replication, digital recording and telephony functions. Audio subsystem 3126 can be configured to receive voice commands from the user.

I/O subsystem 3140 can include touch surface controller 3142 and/or other input controller(s) 3144. Touch surface controller 3142 can be coupled to a touch surface 3146. Touch surface 3146 and touch surface controller 3142 can, for example, detect touch contact and movement (gestures) or break thereof using any of a plurality of touch sensitivity technologies, including but not limited to capacitive, resistive, infrared and surface acoustic wave technologies, as well as other proximity sensor arrays or other elements for determining one or more points of contact with touch surface 3146. Touch surface 3146 can include, for example, a touch screen or the digital crown of a smart watch. I/O subsystem 3140 can include a haptic engine or device for providing haptic feedback (e.g., vibration) in response to commands from processor 3104. In an embodiment, touch surface 3146 can be a pressure-sensitive surface.

Other input controller(s) 3144 can be coupled to other input/control devices 3148, such as one or more buttons, rocker switches, thumb-wheels, infrared ports, Thunderbolt® ports and USB ports. The one or more buttons (not shown) can include an up/down button for volume control of speaker 3128 and/or microphone 3130. Touch surface 3146 or other controllers 3144 (e.g., a button) can include, or be coupled to, fingerprint identification circuitry for use with a fingerprint authentication application to authenticate a user based on their fingerprint(s).

In one implementation, a pressing of the button for a first duration may disengage a lock of the touch surface 3146; and a pressing of the button for a second duration that is longer than the first duration may turn power to the mobile device on or off. The user may be able to customize a functionality of one or more of the buttons. The touch surface 3146 can, for example, also be used to implement virtual or soft buttons.

In some implementations, the mobile device can present recorded audio and/or video files, such as MP3, AAC and MPEG files. In some implementations, the mobile device can include the functionality of an MP3 player. Other input/output and control devices can also be used.

Memory interface 3102 can be coupled to memory 3150. Memory 3150 can include high-speed random access memory and/or non-volatile memory, such as one or more magnetic disk storage devices, one or more optical storage devices and/or flash memory (e.g., NAND, NOR). Memory 3150 can store operating system 3152, such as the iOS operating system developed by Apple Inc. of Cupertino, Calif. Operating system 3152 may include instructions for handling basic system services and for performing hardware dependent tasks. In some implementations, operating system 3152 can include a kernel (e.g., UNIX kernel).

Memory 3150 may also store communication instructions 3154 to facilitate communicating with one or more additional devices, one or more computers and/or one or more servers, such as, for example, instructions for implementing a software stack for wired or wireless communications with other devices. Memory 3150 may include graphical user interface instructions 3156 to facilitate graphic user interface processing; sensor processing instructions 3158 to facilitate sensor-related processing and functions; phone instructions 3160 to facilitate phone-related processes and functions; electronic messaging instructions 3162 to facilitate electronic-messaging related processes and functions; web browsing instructions 3164 to facilitate web browsing-related processes and functions; media processing instructions 3166 to facilitate media processing-related processes and functions; GNSS/Location instructions 3168 to facilitate generic GNSS and location-related processes and instructions; and THz spectroscopy and imaging instructions 3170 to facilitate THz spectroscopy and imaging, as described in reference to FIGS. 1-30.

Each of the above identified instructions and applications can correspond to a set of instructions for performing one or more functions described above. These instructions can be implemented as separate software programs, procedures, or modules or as a single body of code. Memory 3150 can include additional instructions or fewer instructions. Various functions of the mobile device may be implemented in hardware and/or in software, including in one or more signal processing and/or application specific integrated circuits.

The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language (e.g., SWIFT, Objective-C, C#, Java), including compiled or interpreted languages, and it can be deployed in any form, including as a stand-alone program or as a module, component, subroutine, a browser-based web application, or other unit suitable for use in a computing environment.

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable sub combination. Moreover, although features may be described above as acting in certain combinations and even initially claimed as such, one or more features from a claimed combination can in some cases be excised from the combination, and the claimed combination may be directed to a sub combination or variation of a sub combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

As described above, one aspect of the present technology is the gathering and use of data available from various sources to improve the delivery to users of invitational content or any other content that may be of interest to them.

The present disclosure contemplates that in some instances, this gathered data may include personal information data that uniquely identifies or can be used to contact or locate a specific person. Such personal information data can include demographic data, location-based data, telephone numbers, email addresses, home addresses, or any other identifying information.

The present disclosure recognizes that the use of such personal information data, in the present technology, can be used to the benefit of users. For example, the personal information data can be used to deliver targeted content that is of greater interest to the user. Accordingly, use of such personal information data enables calculated control of the delivered content. Further, other uses for personal information data that benefit the user are also contemplated by the present disclosure.

The present disclosure further contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. For example, personal information from users should be collected for legitimate and reasonable uses of the entity and not shared or sold outside of those legitimate uses. Further, such collection should occur only after receiving the informed consent of the users. Additionally, such entities would take any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of advertisement delivery services, the present technology can be configured to allow users to select to "opt in" or "opt out" of participation in the collection of personal information data during registration for services. In another example, users can select not to provide location information for targeted content delivery services. In yet another example, users can select to not provide precise location information, but permit the transfer of location zone information.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, content can be selected and delivered to users by inferring preferences based on non-personal information data or a bare minimum amount of personal information, such as the content being requested by the device associated with a user, other non-personal information available to the content delivery services, or publically available information.

What is claimed is:

1. A method comprising:
   obtaining, from a sensor of an electronic device, sensor data;
   determining, by one or more processors of the electronic device, an orientation of the electronic device based on the sensor data;
   emitting, by a transmitter of the electronic device, an electromagnetic (EM) wave in a terahertz (THz) frequency band, the EM wave being emitted into a dynamic environment that includes a transmission medium that changes over time, wherein the EM wave is emitted according to a power duty cycle that is determined at least in part by the orientation of the electronic device;
   receiving, by a receiver of the electronic device, a reflected EM wave reflected off at least one object in the environment;
   determining, by the one or more processors of the electronic device, a spectral response of a received signal indicative of the reflected EM wave, the spectral response including absorption spectra at a frequency in the THz frequency band that is indicative of the transmission medium in the environment;
   comparing, by the one or more processors, the absorption spectra with known absorption spectra of target transmission mediums;
   identifying, by the one or more processors and based on results of the comparing, a particular target transmission medium as being the transmission medium in the environment; and
   determining, by the one or more processors, a concentration level of the identified target transmission medium in the environment.

2. The method of claim 1, wherein the orientation indicates that the transmitter of the electronic device is pointing to a ceiling or a floor of the environment.

3. The method of claim 2, further comprising:
   determining from the sensor data whether the electronic device is stationary;
   in accordance with the electronic device being stationary, emitting the EM wave according to a first power duty cycle; and
   in accordance with the electronic device not being stationary, emitting the EM wave according to a second power duty cycle that is different than the first power duty cycle.

4. The method of claim 3, further comprising:
   in accordance with the first power duty cycle, configuring, by the one or more processors, the transmitter to use a first number of antenna elements for emitting the EM wave into the dynamic environment; and
   in accordance with the second power duty cycle, configuring, by the one or more processors, the transmitter to use a second number of antenna elements for emitting the EM wave into the environment, wherein the second number of antenna elements is different than the first number of antenna elements.

5. The method of claim 1, wherein determining a concentration level of the identified target transmission medium in the environment, further comprises:
   determining an absorption loss from the absorption spectra in the spectral response of the received signal;
   determining a path length of the received signal; and
   using the absorption loss and the path length to obtain the concentration level from a reference library of known concentration levels.

6. A method comprising:
emitting, by a transmitter of an electronic device, an electromagnetic (EM) wave in a terahertz (THz) frequency band into a dynamic environment, the emitting including sweeping transmission of the EM wave through a plurality of angles;
for each angle of the plurality of angles:
  receiving, by a receiver of the electronic device, an EM wave reflected from the environment;
  determining, by the receiver, a first received signal strength of the received EM wave; and
  storing the angle and first received signal strength in a data structure that includes a plurality of angles and corresponding received signal strengths;
determining, from the plurality of angles, a particular angle having the highest received signal strength;
adapting the transmitter to emit the EM wave in accordance with the particular angle;
receiving, by the receiver, a reflected EM wave reflected off at least one object in the environment;
determining, by one or more processors of the electronic device, a spectral response of a received signal indicative of the reflected EM wave, the spectral response including absorption spectra at a frequency in the THz frequency band that is indicative of the transmission medium in the environment;
comparing, by the one or more processors, the absorption spectra with known absorption spectra of target transmission mediums;
identifying, by the one or more processors and based on results of the comparing, a particular target transmission medium as being the transmission medium in the environment; and
determining, by the one or more processors, a concentration level of the identified target transmission medium in the environment.

7. The method of claim 6, further comprising:
obtaining from a sensor of the electronic device, sensor data;
determining, by the one or more processors, whether the electronic device has moved based on the sensor data;
determining a second received signal strength for the particular angle; and
in accordance with the second receive signal strength for the particular angle being higher than the first received signal strength for the particular angle, replacing the first received signal strength in the data structure with the second received signal strength.

8. A method comprising:
emitting, by a transmitter of an electronic device, an electromagnetic (EM) wave in a terahertz (THz) frequency band, the EM wave being emitted into a dynamic environment that includes a transmission medium that changes over time, wherein the EM wave is emitted at discrete frequencies corresponding to known absorption frequencies of known transmission mediums;
receiving, by a receiver of the electronic device, a reflected EM wave reflected off at least one object in the environment;
determining, by one or more processors of the electronic device, a spectral response of a received signal indicative of the reflected EM wave, the spectral response including absorption spectra at a frequency in the THz frequency band that is indicative of the transmission medium in the environment;
comparing, by the one or more processors, the absorption spectra with known absorption spectra of target transmission mediums;
identifying, by the one or more processors and based on results of the comparing, a particular target transmission medium as being the transmission medium in the environment; and
determining, by the one or more processors, a concentration level of the particular target transmission medium in the environment.

9. The method of claim 8, wherein the EM wave is emitted at discrete frequencies by adjusting a resonance frequency of an emitter circuit of the transmitter to resonate at each discrete frequency during a scan cycle.

10. An electronic device, comprising:
a sensor;
a transmitter configured to emit an electromagnetic (EM) wave in a terahertz (THz) frequency band, the EM wave being emitted into a dynamic environment that includes a transmission medium that changes over time, wherein the EM wave is emitted according to a power duty cycle that is determined at least in part by an orientation of the electronic device;
a receiver configured to receive a reflected EM wave reflected off at least one object in the environment;
one or more processors;
memory storing instructions that when executed by the one or more processors, cause the one or more processors to perform operations comprising:
  obtaining sensor data from the sensor;
  determining the orientation of the electronic device based on the sensor data;
  determining a spectral response of the reflected EM wave, the spectral response including absorption spectra at a frequency in the THz frequency band that is indicative of the transmission medium in the environment;
  comparing the absorption spectra with known absorption spectra of target transmission mediums;
  identifying, based on results of the comparing, a particular target transmission medium as being the transmission medium in the environment; and
  determining a concentration level of the identified target transmission medium in the environment.

11. The electronic device of claim 10, wherein the orientation indicates that the transmitter is pointing to a ceiling or a floor of the environment.

12. The electronic device of claim 11, further comprising:
determining from the sensor data whether the electronic device is stationary;
in accordance with the electronic device being stationary, emitting the EM wave according to a first power duty cycle; and
in accordance with the electronic device not being stationary, emitting the EM wave according to a second power duty cycle that is different than the first power duty cycle.

13. The electronic device of claim 12, further comprising:
in accordance with the first power duty cycle, configuring, by the one or more processors, the transmitter to use a first number of antenna elements of the electronic device for emitting the EM wave into the dynamic environment; and
in accordance with the second power duty cycle, configuring, by the one or more processors, the transmitter to use a second number of antenna elements of the electronic device for emitting the EM wave into the environment, wherein the second number of antenna elements is different than the first number of antenna elements.

14. The electronic device of claim 10, wherein determining a concentration level of the identified target transmission medium in the environment, further comprises:
    determining an absorption loss from the absorption spectra in the spectral response of a received signal;
    determining a path length of the received signal; and
    using the absorption loss and the path length to obtain the concentration level from a reference library of known concentration levels.

15. An electronic device, comprising:
    a sensor;
    a transmitter configured to emit an electromagnetic (EM) wave in a terahertz (THz) frequency band into a dynamic environment, the emitting including sweeping transmission of the EM wave through a plurality of angles;
    a receiver configured to, for each angle of the plurality of angles, receive an EM wave reflected from the environment, and to determine a first received signal strength of the received EM wave;
    one or more processors configured to:
        store the angle and first received signal strength in a data structure that includes a plurality of angles and corresponding received signal strengths; and
        determine, from the plurality of angles, a particular angle having the highest received signal strength;
        adapt the transmitter to emit the EM wave in accordance with the particular angle;
        determine a spectral response of a received signal indicative of the reflected EM wave, the spectral response including absorption spectra at a frequency in the THz frequency band that is indicative of the transmission medium in the environment;
        compare the absorption spectra with known absorption spectra of target transmission mediums;
        identify, based on results of the comparing, a particular target transmission medium as being the transmission medium in the environment; and
        determine a concentration level of the identified target transmission medium in the environment.

16. The electronic device of claim 15, further comprising:
    obtaining sensor data from the sensor;
    determining, by the one or more processors, whether the electronic device has moved based on the sensor data;
    determining, by the receiver, a second received signal strength for the particular angle; and
    in accordance with the second receive signal strength for the particular angle being higher than the first received signal strength for the particular angle, replacing the first receive signal strength in the data structure with the second receive signal strength.

17. An electronic device, comprising:
    a transmitter configured to emit an electromagnetic (EM) wave in a terahertz (THz) frequency band, the EM wave being emitted into a dynamic environment that includes a transmission medium that changes over time, wherein the EM wave is emitted at discrete frequencies corresponding to known absorption frequencies of known transmission mediums;
    a receiver configured to receive a reflected EM wave reflected off at least one object in the environment;
    one or more processors configured to:
        determine a spectral response of a received signal indicative of the reflected EM wave, the spectral response including absorption spectra at a frequency in the THz frequency band that is indicative of the transmission medium in the environment;
        compare the absorption spectra with known absorption spectra of target transmission mediums;
        identify, based on results of the comparing, a particular target transmission medium as being the transmission medium in the environment; and
        determine a concentration level of the particular target transmission medium in the environment.

18. The electronic device of claim 17, wherein the EM wave is emitted at discrete frequencies by adjusting a resonance frequency of an emitter circuit of the transmitter to resonate at each discrete frequency during a scan cycle.

* * * * *